(12) United States Patent
Schenker et al.

(10) Patent No.: US 10,137,253 B2
(45) Date of Patent: Nov. 27, 2018

(54) INJECTION DEVICE WITH DOSE INDICATOR AND SPRING DRIVE

(71) Applicant: TecPharma Licensing AG, Burgdorf (CH)

(72) Inventors: Susanne Schenker, Langenthal (CH); Ursina Streit, Schonbuhl (CH)

(73) Assignee: TECPHARMA LICENSING AG, Burgdorf (CH)

( * ) Notice: Subject to any disclaimer, the term of this patent is extended or adjusted under 35 U.S.C. 154(b) by 428 days.

(21) Appl. No.: 14/501,739

(22) Filed: Sep. 30, 2014

(65) Prior Publication Data

US 2015/0018771 A1    Jan. 15, 2015

Related U.S. Application Data

(63) Continuation of application No. PCT/EP2013/056103, filed on Mar. 22, 2013.

(30) Foreign Application Priority Data

Mar. 30, 2012  (EP) ..................................... 12162777
Aug. 1, 2012  (EP) ..................................... 12178912

(51) Int. Cl.
*A61M 5/315* (2006.01)
*A61M 5/20* (2006.01)
(Continued)

(52) U.S. Cl.
CPC ............ *A61M 5/3156* (2013.01); *A61M 5/20* (2013.01); *A61M 5/31553* (2013.01);
(Continued)

(58) Field of Classification Search
CPC .. A61M 5/3156; A61M 5/20; A61M 5/31553; A61M 5/31563; A61M 5/31583;
(Continued)

(56) References Cited

U.S. PATENT DOCUMENTS

| | | |
|---|---|---|
| 5,104,380 A | 4/1992 | Holman et al. |
| 2006/0153693 A1 | 7/2006 | Fiechter |

(Continued)

FOREIGN PATENT DOCUMENTS

| | | |
|---|---|---|
| WO | WO 2001/019434 | 3/2001 |
| WO | 2006045528 A1 | 5/2006 |

(Continued)

*Primary Examiner* — Amber Stiles
(74) *Attorney, Agent, or Firm* — Dorsey & Whitney LLP

(57) ABSTRACT

A driving and dosing device for an injection device for administering a liquid product, in particular a medication, wherein a product dose to be administered can be set by means of the driving and dosing device, comprising: a) a housing, b) a dose indicating element, around the circumference of which a dose scale is arranged, c) a pointing device and a (d) dosing element that can be gripped in particular by the user of the driving and dosing device, wherein the dose indicating element can be rotated, in particular screwed, relative to the pointing device and about an axis of rotation (L) and a value of the dose scale that corresponds to the set dose can be read by means of the pointing device, in order to set the dose to be administered by rotating the dosing element relative to the pointing device, and e); a discharge spring, which stores the energy required for discharging the product, wherein the discharge spring is loaded by means of rotation of the dosing element.

20 Claims, 9 Drawing Sheets

(51) Int. Cl.
*A61M 5/24* (2006.01)
*A61M 5/31* (2006.01)

(52) U.S. Cl.
CPC .... *A61M 5/31563* (2013.01); *A61M 5/31583* (2013.01); *A61M 5/3157* (2013.01); *A61M 2005/2407* (2013.01); *A61M 2005/3126* (2013.01); *A61M 2205/581* (2013.01); *A61M 2205/582* (2013.01)

(58) Field of Classification Search
CPC ........ A61M 5/3157; A61M 2005/2407; A61M 2005/3126; A61M 2205/581; A61M 2205/582
See application file for complete search history.

(56) References Cited

U.S. PATENT DOCUMENTS

| | | |
|---|---|---|
| 2006/0206057 A1 | 9/2006 | DeRuntz |
| 2006/0276753 A1 | 12/2006 | Kronestedt |
| 2008/0306445 A1* | 12/2008 | Burren .................... A61M 5/24 604/136 |
| 2009/0012479 A1 | 1/2009 | Moller |
| 2009/0054839 A1* | 2/2009 | Moller .............. A61M 5/14566 604/135 |
| 2010/0168677 A1 | 7/2010 | Gabriel |
| 2010/0268171 A1 | 10/2010 | Moller |
| 2010/0274198 A1 | 10/2010 | Bechtold |
| 2010/0324493 A1* | 12/2010 | Plumptre .......... A61M 5/31541 604/207 |
| 2012/0010575 A1 | 1/2012 | Jones |
| 2015/0018776 A1 | 1/2015 | Schenker |
| 2016/0184530 A1 | 6/2016 | Schenker |

FOREIGN PATENT DOCUMENTS

| | | |
|---|---|---|
| WO | WO 2006/077466 | 7/2006 |
| WO | WO 2008/031237 | 3/2008 |
| WO | WO 2008/087071 | 7/2008 |
| WO | WO 2010/081489 | 7/2010 |
| WO | WO 2010/115670 | 10/2010 |
| WO | WO 2010/149209 | 12/2010 |
| WO | 2011045611 A2 | 4/2011 |
| WO | WO 2012/037938 | 3/2012 |

* cited by examiner

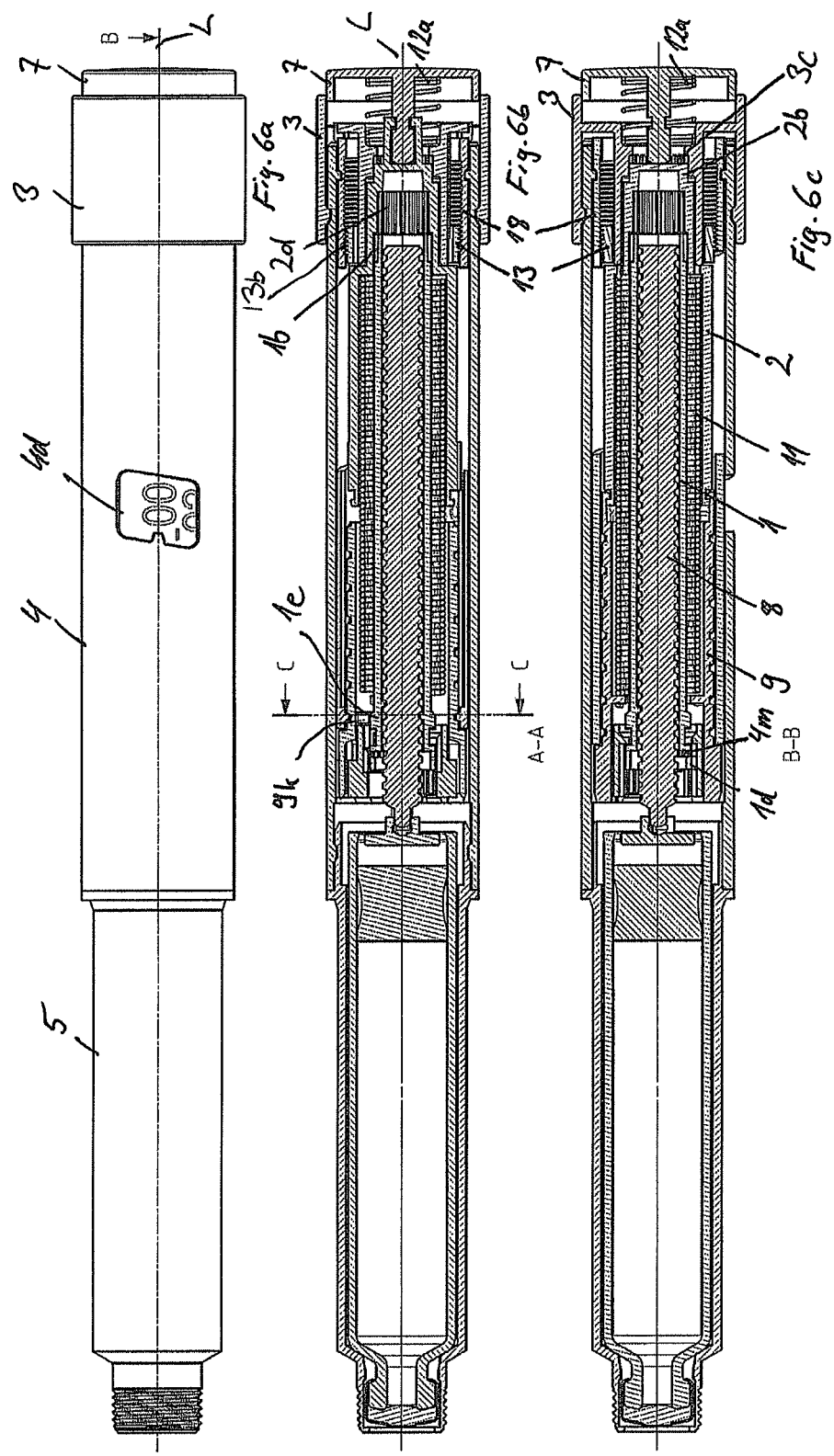

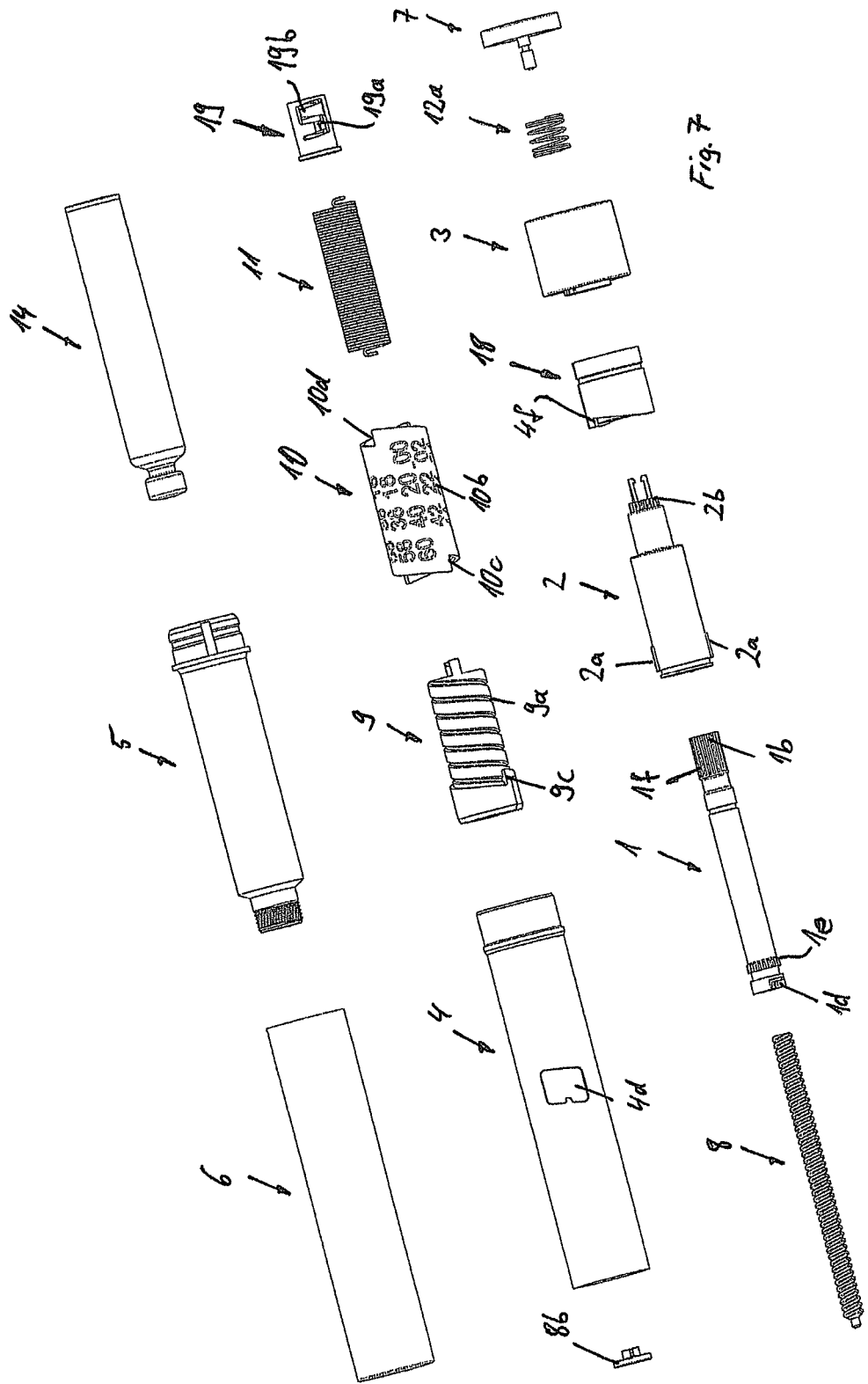

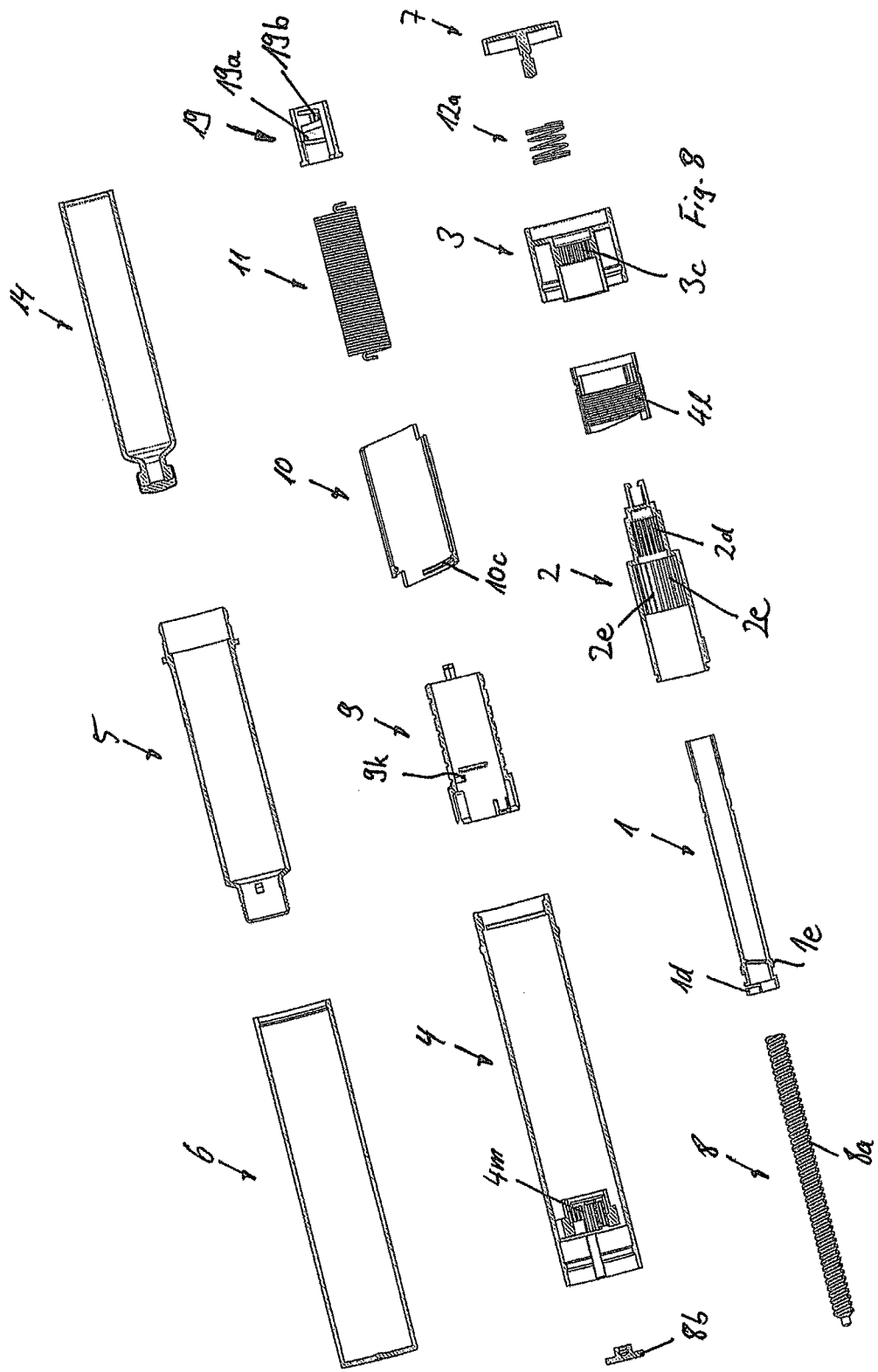

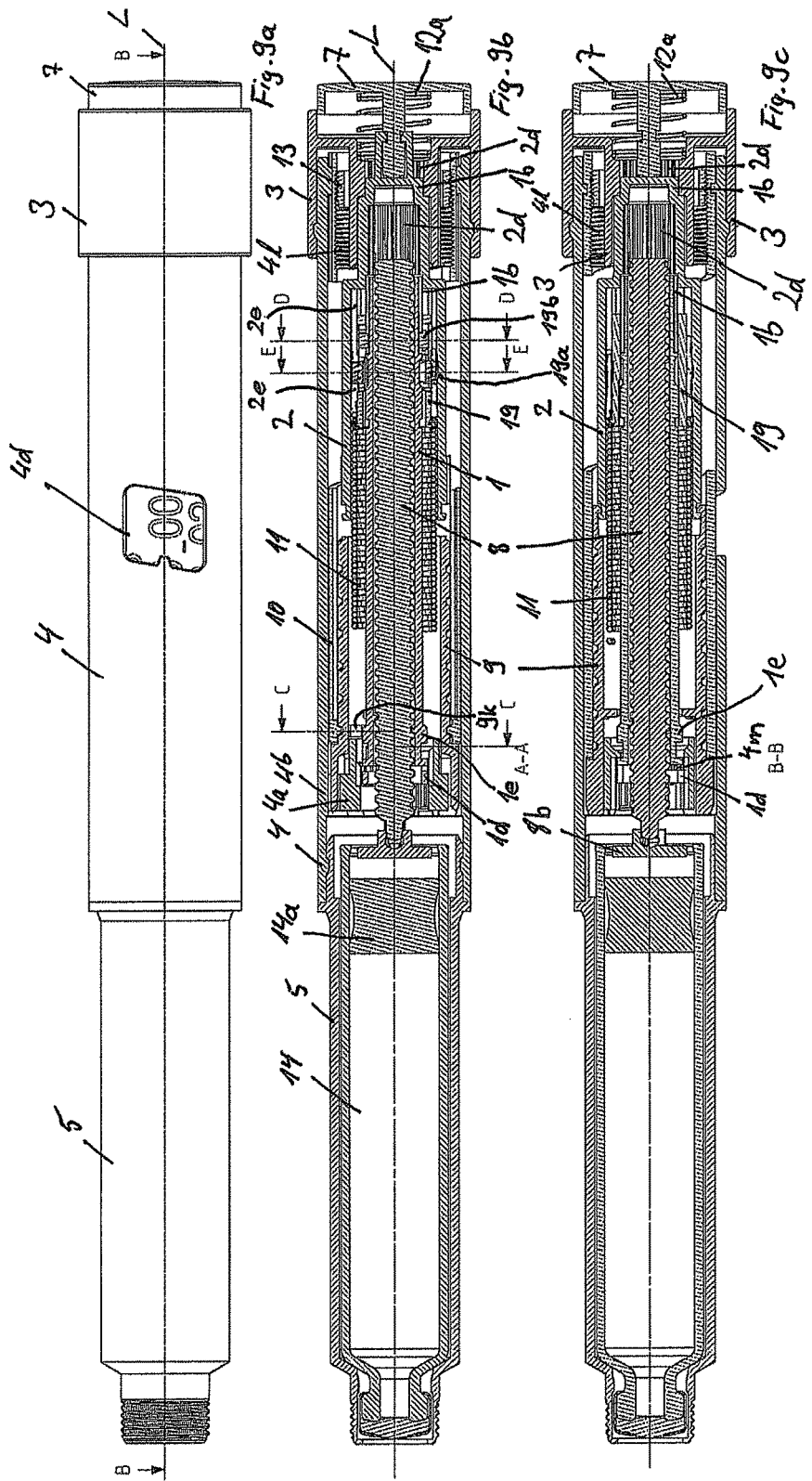

INJECTION DEVICE WITH DOSE INDICATOR AND SPRING DRIVE

CROSS-REFERENCE TO RELATED APPLICATIONS

This application is a Continuation of International Patent Application No. PCT/EP2013/056103 filed Mar. 22, 2013, which claims priority to European Patent Application No. EP 12 162 777.2 filed Mar. 30, 2012 and European Patent Application No. 12 178 912.7 filed Aug. 1, 2012, the entire contents of each are incorporated herein by reference.

BACKGROUND

The invention relates to an injection device for administering a liquid product, particularly a medicine, such as insulin for diabetes therapy. In particular, the invention relates to a driving and dosing device for such an injection device.

An injection device having a dose indicating drum and a drive spring is known from the prior art, namely WO 2008/031237 A1. The drive spring is a coiled spring, which is wound in a spiral shape from a strip-shaped material. When the product dose is being set, the spring is tensioned with a rotational movement. In order to inject a dose, a piston rod is coupled to the spring by means of an actuating button at the proximal end of the device, whereby the spring can output the energy stored therein to the piston rod, whereby the piston rod is moved in the discharge direction. To set a new dose, the spring is again cocked by rotating the dosing knob, and so on. This is repeated until the product container has been emptied.

An injection device with a helical spring is also known from U.S. Pat. No. 5,104,380 A, the spring being likewise cocked rotationally during dosing, so that the helical spring can also be referred to as a torsion spring. The spring, cocked by rotation before each product discharge, transfers its energy to the piston rod in order to propel the piston rod.

WO 2006/77466 A2 discloses an injection device that has a direct mechanical drive between the person applying the injection force and the piston rod, which is displaced in the distal direction for the injection of the medicine.

SUMMARY

One problem addressed by the invention is that of specifying a driving and dosing device for an injection device with an improved dose indication and which in particular gives the user of the device better information about the operating condition of the device.

This problem is solved by the features of claim 1. Further refinements follow from the dependent claims, the description and the figures.

The invention proceeds from a drive mechanism for an injection device for administering a liquid medicine or product. The drive mechanism has a housing. The housing is preferably sleeve-shaped and/or elongated in shape. The housing can extend along a longitudinal axis, for example.

The housing can optionally accommodate a product container or can itself constitute the product container. The housing can be in one or more parts. For example, the housing can form a proximal housing part that comprises or has the driving and dosage device. The housing can additionally have a product container holder, which receives the product container such as a carpule and is connected to the housing or the proximal housing part. This connection can be such that the product container holder and the housing or the proximal housing part is non-detachable after connection, i.e. only detachable by destroying connecting elements. Such a solution is particularly advantageous for single-use injection devices, which can be disposed of as a whole after the product contained in the product container has been completely discharged. Alternatively, the product container holder can also be detachably connected to the housing, whereby it is possible, although also less preferred, to use the driving and dosing device several times if necessary, i.e. to replace an empty product container with a filled product container.

The housing is principally used in order to be gripped by the user of the device. In particular, the housing can have a substantially cylindrical shape. The housing can have a pointing device, particularly a window, by means of which or through which the currently set dosage can be read out, preferably from a scale of the dose setting element.

The driving and dosing device, which in particular forms an injection device together with the container, comprises a dose indicating element, across the periphery of which a dose scale is arranged, in addition to a housing. The dose indicating element can be annular in cross section, for example. The dose indicating element can be a dose indicating drum or a dose indicating ring, for example. The dose scale can extend over the periphery of the dose indicating element, preferably in a helical shape. The dose scale preferably comprises a plurality of values, which are arranged one after another and produce the dose scale. These are preferably numerical values that indicate the desired product dose in international units (IU).

Alternatively, the dose scale can be arranged without a pitch over the periphery of the dose indicating element, such as the dose indicating ring, in which case the scale values then repeat after a revolution of the dose indicating element. In a dose scale with a pitch, i.e. a helical dose scale, the dose indicating element, particularly the dose indicating drum, can be rotated more than one revolution without the scale values repeating, whereby higher or more scale values can advantageously be represented.

The driving and dosing device further comprises a pointing device, wherein the dose indicating element, in order to set the dose, can be rotated relative to the pointing device and particularly about a rotational axis that preferably corresponds to the longitudinal axis of the driving and dosing device or/and the dose indicating element. This movement can be a purely rotational movement, i.e. a rotational movement without superimposed axial movement. Preferably an axial movement is superimposed on the rotational movement, whereby the dose indicating element is screwable relative to the pointing device in order to set the dose to be administered. A screwable dose indicating element can be advantageously combined with a helical dose scale, the screwing movement and the dose scale preferably having the same pitch. A dose indicating element without axial movement can be advantageously combined with a pitch-free dose scale.

A value of the dose scale that corresponds to the set dose can be read out by means of the pointing device, which is preferably formed on the housing. The pointing device can be a window, for example, which can be formed by an opening in the housing or by a transparent insert. Alternatively or optionally, the pointing device can be an arrow or have an arrow, which marks the value of the dose scale corresponding to the set dose in addition to the window. This is advantageous if a second value appears in the window, at least partially, in order to ensure an unambiguous choice of dose, for example. The pointer can be a protrusion or an imprint or a notch or the like.

The driving and dosing device comprises a dosing element, which can be formed as a dosing knob for example, and can optionally be referred to as a setting element. The dosing element can preferably be gripped by the user (patient, physician, medical assistance personnel) of the driving and dosing device and preferably constitutes an external, more particularly externally accessible, surface of the driving and dosing device. To adjust the dose to be discharged or administered, the dosing element is preferably gripped by the user and rotated relative to the housing, and in particular relative to the pointing device, about an axis of rotation, which preferably corresponds to the longitudinal axis of the driving and dosing device, which is designed in an elongated shape for example. The dosing element is preferably connected axially fixedly to the housing, more particularly secured against displacement along a longitudinal axis of the housing, whereby the intuitive handling of the device by the user is advantageously facilitated, because the user needs only to carry out a rotational movement of the dosing element to adjust the dose.

In particular, the dose indicating element can be secured against rotation at least during the dose-setting, but connected or coupled to the dosing element so as to be axially displaceable. For intuitive operation, it is advantageous if, when the dosing element is rotated by a given angle of rotation, the dose indicating element is rotated by the same angle of rotation.

The driving and dosing device can have an actuating element, e.g. in the form of an actuating button. The actuating element can form an outer surface of the driving and dosing device and/or can be accessible from the outside. The actuating element can be formed on the proximal end, in particular the rear end, of the driving and dosing device or can constitute this end. In this manner, the actuating element can advantageously be actuated, particularly pressed, with the thumb of the hand that is gripping the housing. The actuation can be ended by releasing the actuating element. "Actuating" is understood to mean the displacement of the actuating element into the driving and dosing device, more particularly in the distal direction, which can affect the discharging of a product. The actuating element is advantageously displaceable relative to the dosing element and in particular can be received by the dosing element so as to be displaceable axially.

The actuating element can advantageously be displaceable, more particularly actuatable, against the force of at least one spring, particularly a return or coupling spring, whereby this at least one spring is cocked (i.e., twisted, tensioned, compressed or otherwise manipulated to store energy). By being released, this spring can reset the actuating element, more particularly displace it relative to the dosing element, specifically in the proximal direction or out of the driving and dosing device. A first reset spring can be arranged between the actuating element and the dosing element and be supported thereon, for example. Alternatively or additionally, a second reset spring can be arranged between a bearing element and the product container or the product container holder and be supported thereon, for example.

The driving and dosing device further comprises a bearing element, with which the dose indicating element is engaged. This engagement advantageously effects the rotational or screwing movement of the dose indicating element relative to the pointing device. For example, the engagement between the dose indicating element and the bearing element can be a threaded engagement. In particular, the bearing element can have an external thread and the dose indicating element an internal thread, these threads engaging with one another and thereby causing the dose indicating element to be screwable relative to the bearing element. The bearing element can be connected rotationally fixedly to the housing for example, or have a rotationally fixed engagement with the housing, it being preferred that the bearing element is axially displaceable relative to the housing.

The dose indicating element can be rotated or screwed between a maximum dose position and a zero dose position. In the zero dose position, the dose or the digit "0" can advantageously be readable in the pointing device. In the maximum dose position, the maximum product dose that can be discharged with the driving and dosing device can advantageously be readable.

The dose indicating element can be blocked in the zero dose position against rotation in one rotational direction, namely the rotational direction that would cause a dose of less than zero to be set. In the zero position, the display element can preferably only be rotated in a direction of rotation that causes an increase of the dose. In the maximum dose position, the dose indicating element is preferably blocked against rotation in one rotational direction, namely the rotational direction that would cause the setting of a dose greater than the maximum settable dose. Preferably, the dose indicating element in the maximum dose position can only be rotated in the direction that causes a reduction of the product dose.

For example the dose indicating element can have a stop that strikes against a mating stop in the zero dose position and thus prevents rotation in one rotational direction. The same or an additional stop on the dose indicating element can prevent rotation of the dose indicating element past the maximum dose. In particular, an additional mating stop, namely a maximum dose mating stop, can be provided for this purpose. The other mating stop can accordingly be referred to as the zero dose mating stop. Thus the dose indicating element can have a zero dose stop for the zero dose mating stop and a maximum dose stop for the maximum dose mating stop. The stop or the stops are preferably active in the circumferential direction and/or in the axial direction.

The bearing element is preferably displaceable together with the dose indicating element relative to the housing and along the axis of rotation, more particularly in the distal direction. Alternatively, the dose indicating element can have a thread that is engaged with the housing. Thereby the dose indicating element can be displaced back and forth relative to the housing but not independently of the screwing movement, particularly not with a purely axial movement.

The actuating element is preferably coupled to the bearing element in such a manner that a displacement of the actuating element relative to the housing and/or the dosing element causes a displacement of the bearing element relative to the housing and/or the dosing element, particularly along the longitudinal axis of the driving and dosing device.

Because the dose indicating element is preferably engaged with the bearing element and the bearing element can be displaced relative to the housing and along the axis of rotation, the dose indicating element can also be displaced relative to the housing and along the axis of rotation independently of the rotating or screwing movement that the dose indicating element undergoes during setting of the dose.

The fact that the bearing element has been displaced together with the dose indicating element can advantageously be read out on the pointing device or the dose indicating element. In this way, the user can monitor the operating status of the driving and display device, i.e. whether the driving and display device, and in particular the actuating element, is or is not actuated for a discharge.

In a preferred variant, the actuating element or/and the bearing element can be displaceable together with the dose indicating element relative to the pointing device, the housing and along the axis of rotation. In the area of the pointing device, particularly in the window of the pointing device, a marking different from the dose scale can appear when the bearing element has been displaced. The marking is preferably arranged on the dose indicating element. If the bearing element has not been displaced, more particularly the driving and dosing device or the actuating element has not been actuated for discharging the product, the marking can be arranged outside the pointing device, for example concealed by a housing or some other element. If the bearing element has been displaced, in particular if the driving and dosing device has been actuated for discharging the product, the marking can emerge from the covered area, so that it appears or is readable on or in the pointing device. If the actuation of the driving and dosing device has been interrupted or terminated, the bearing element can return to the original position, whereby the marking preferably is removed from the area of the pointing device and in particular is concealed.

During actuating of the driving and dosing device in order to discharge a product, the first and/or the second coupling or reset spring can be cocked (i.e., twisted, tensioned, compressed or otherwise manipulated to store energy). In other words, the bearing element can be displaced during actuation against the force of this at least one spring, more particularly from a non-actuated position into an actuated position. The spring can be a helical spring or a coil spring, for example, acting as a compression spring. This spring has the further effect of resetting the bearing element to the starting position or non-actuated position if the actuation is interrupted or ended. In particular, the bearing element is displaced in the distal direction during actuation. The bearing element is pushed back into its original position by means of the spring if the actuation is interrupted or ended.

Actuating the actuating element has the effect in particular of displacing the bearing element together with the dose indicating element relative to the housing and along the axis of rotation. In the broader sense, the actuation of the actuating element can displace a propulsion element, the distal end of which is provided to act in the distal direction, more particularly the discharging direction, on a piston of the product container mounted or mountable on the driving and dosing device. The actuating element can be arranged at the proximal end, i.e. rear end, of the driving and dosing device or can form the proximal end of the driving and dosing device. Alternatively, the actuating element can be arranged laterally on the housing and/or between the distal end and the proximal end of the driving and dosing device. In general, the actuating element can be formed in the manner of an actuating button. During actuation, the actuating element is preferably displaced relative to the housing or the dosing element. In particular, the user of the device can advantageously actuate the actuating element with the thumb of the hand that is gripping the housing of the driving and dosing device, for example.

The actuating element is preferably connected to the bearing element in such a manner that it displaces the bearing element during actuation, more particularly via a clutch element which can be connected axially fixedly and rotatably to the bearing element for example. Alternatively to an axially fixed connection, the clutch element can alternatively loosely strike the bearing element (and vice versa) so that the clutch element can drive the bearing element and vice versa.

In preferred embodiments, the bearing element has at least one resiliently arranged catch, against which a clutch element strikes at an impact point, more particularly on the end face, when the actuating element is actuated for discharging a product. The catch can be deflected elastically by means of the dose indicating element out of the position in which it is arranged in front of the bearing element, and the bearing can strike against the catch. Due to the deflection of the bearing element, preferably toward the longitudinal axis of the device, the bearing element is displaceable toward the clutch element or/and the catch is displaceable past the impact point, more particularly axially displaceable, particularly when the actuating element is actuated. The displacement can be caused, for example, by the reset spring or one of the reset springs, such as the second reset spring, acting on the bearing element. The bearing element advantageously strikes against a stop during this movement, and therefore a tactile and/or acoustic signal such as an individual or single click noise is generated, which signals the end of the product discharge to the user, for example.

The dose indicating element preferably has, on its inner periphery for example, a projection, particularly a cam, which is arranged such that it deflects the catch shortly before the dose indicating element reaches its zero dose position, more particularly strikes against the zero dose mating stop. The signal generation is simplified in this way. The cam can deflect the catch, e.g. if the dose that can be read in the pointing device is less than 10 IU, preferably less than 5 or less than or equal to 2 IU. The catch is preferably deflected when 1 or 2 IU is passing through the pointing device, more particularly being counted down.

In generally preferred embodiments, the actuation of the actuating element can cause the dose indicating element to be rotated, particularly screwed, relative to or on the bearing element or the housing, more particularly in a direction such that the values moving past the pointing device during the rotational movement count down on the dose scale. The angle of rotation of the dose indicating element and the discharge stroke of the propulsion element preferably have a proportional relationship, more particularly at every point during the dose discharging. This makes it possible to implement a real-time display, which counts down during dose discharging until it finally reaches the value 0, at which point the discharging of the dose in question is complete. If the actuation for discharging is interrupted during the back-rotation of the dose indicating element, the dose indicating element indicates the remaining amount necessary for the discharging of this dose.

In a preferred alternative variant, the drive and dosing device can be designed such that the energy required for the back-rotation of the dose indicating element or/and the displacement of the propulsion element in the distal direction is exerted automatically, more particularly by means of a spring contained in the driving and dosing device, in particular a discharge spring, in which the required energy is or can be stored. For example, the spring energy stored in the discharge spring can be output upon actuation of the actuating element to the dose indicating element or/and the propulsion element, so that the dose indicating element is rotated back and the propulsion element is displaced in the distal direction. The discharge spring is preferably coupled to the dosing element, particularly via a detachable coupling, in such a manner that a rotation of the dosing element during dose-setting, particularly during a dose increase or a rotation in the first rotational direction, cocks the discharge spring. The discharge spring can then store the energy required for the set dosage.

Rotation of the dosing element in a second direction, which causes a dose reduction, can either cause the discharge spring to be relaxed or not relaxed. If the discharge spring is to be relaxed during rotation of the dosing element in the second rotational direction, one end of the spring can be coupled to the dosing element rotationally fixedly in both rotational directions, more particularly by the clutch. If the discharge spring is not to be discharged during rotation of the dosing element in the second rotational direction, it is advantageous to arrange a unidirectional coupling, particularly a ratchet, kinematically between the dosing element and the spring, in addition to the aforementioned clutch, the ratchet transmitting rotation of the dosing element in the first direction to the discharge ring and not transmitting rotation of the dosing element in the second direction to the discharge spring.

In order to prevent the discharge spring cocked by the rotation of the dosing element from outputting its stored energy to the dosing element, whereby the dosing element would automatically be rotated back in the second direction when released, a ratchet, more particularly a ratchet spring acting according to the principle of a slip clutch, is preferably arranged between the dosing element and the housing. The ratchet is designed such that it generates a torque inhibiting the rotation of the dosing element, which is greater than the torque exerted by the maximally cocked discharge spring on the dosing element in the maximum dose position of the dose indicating element. The dosing element can only be rotated by additional exertion of a torque by the user.

The ratchet can comprise a ratchet spring, which is connected rotationally fixedly to the dosing element, for example, or is fixed to the dosing element and engages with toothing, particularly a front toothing, of the housing. The toothing has one or more teeth arranged across the circumference, which are preferably spaced apart from one another at a pitch such that each pitch corresponds to 1 IU or 2 IU. The ratchet spring can press engagement cams against the toothing, wherein the engagement cams snap over the toothing when the dosing element is rotated, more particularly in the 1 IU or 2 IU steps. The ratchet spring can form the engagement cams, for example, and/or be annular or/and can be a punched bent part, which is punched from a plate-like semifinished product, for example.

The dosing element, more particularly the dosing knob, can surround or receive the actuating element, specifically the actuating button. Thus the dosing element and the actuating element can form the proximal end of the driving and dosing device. The actuating element is preferably displaceable relative to the dosing element for actuation.

The driving and dosing device can comprise a propulsion element, the distal end of which is provided to act on a piston, in particular indirectly or preferably directly. The piston can be part of a product container such as a carpule mounted or mountable on the driving and dosing device. In a broader sense, the propulsion element can be referred to or designed as a piston rod, wherein the propulsion element need not necessarily be solid, but can also be hollow, e.g. sleeve-shaped. A flange, rotatable for example, that presses against the piston, can optionally be arranged at the distal end of the propulsion element. It is generally preferred that the distal end of the propulsion element presses against the piston. The propulsion element is preferably displaceable relative to the housing along the longitudinal axis of the driving and dosing device.

The propulsion element preferably has an external thread and a longitudinal guide superimposed on the external thread, wherein the device has a rotation element that engages either with the longitudinal guide or the thread, the respective other of these two elements being engaged rotationally fixedly with the housing or an element fixed relative to the housing. The rotation element is preferably arranged axially fixedly in the housing. If the rotation element engages with the longitudinal guide, the propulsion element is rotated along with the rotation element, whereby the rotation element screws along its longitudinal axis due to the threaded engagement. If the rotation element engages with the thread, the propulsion element is screwed relative to the rotation element, whereby the rotation element is displaced along its longitudinal axis due to the rotationally fixed engagement with the housing or the element fixed relative to the housing.

The element, particularly an inner sleeve, engaging with the rotation element can preferably surround the propulsion element in a sleeve-like manner and/or can be fixed relative to the housing or formed by the housing. An annular gap can be formed between this sleeve-shaped housing part and the external, preferably also sleeve-shaped, housing part, which brings the advantage that an optionally present dose indicating element, particularly an indicating drum, can be received therein. This results in that the length of the driving and dosing device can be kept small.

Rotation of the rotation element has the effect, in particular, that the spring outputs energy to the propulsion element, whereby the propulsion element is moved in the distal direction. The rotation of the rotation element about a defined angle of rotation causes the advancement of the propulsion member by a defined discharge stroke. By selectively releasing or blocking rotation of the rotation element relative to the housing, the discharge spring can be allowed to move the propulsion element in the distal direction relative to the housing, or not to move it. In particular, the rotation element can be coupled to the actuating element such that, upon actuation of the actuating element for a product discharge, the rotation element is released for a rotation relative to the housing in order to discharge the product, and it is blocked from rotation relative to the housing if the actuating element is not actuated. In particular, a clutch that effects the release and locking of rotation of the rotation element relative to the housing can be arranged between the actuating element and the rotation element.

The clutch can advantageously release the rotation of the rotation element relative to the housing if the actuating element is actuated, and can block the rotation of the rotation element relative to the housing when the actuating element is released.

It is advantageous that the rotation element is connected to the housing by means of a ratchet. The rotation element can have a resilient catch element on its periphery and/or at its distal end that engages with toothing extending over the periphery, particularly internal toothing formed by the housing, or an element, such as an inner sleeve of the housing, that is fixed relative to the housing. This has the effect, on the one hand, that a certain torque must be exerted on the rotation element in order to rotate the rotation element relative to the housing, and on the other, that the rotation of the rotation element is signaled by clicking noises. Thus the product discharge can be signaled to the user by the rotating rotation element.

The dose indicating element, particularly the dose indicating drum, can be rotatable relative to the rotation element during the setting of a dose, i.e. in the non-actuated state of the driving and dosing device or the actuating element. The dose indicating element is preferably rotationally fixed relative to the rotation element during the actuation of the device in order to discharge the product dose and is axially movable, for example, or is rotationally fixedly connected to the rotation element, in particular with the above-described clutch or some other clutch.

The driving and dosing device can have a first clutch, for example, more particularly a discharge clutch, which is opened when the actuating element is non-actuated and closed when the actuating element has been actuated, or is closed by the actuation of the actuating element. With the clutch opened, the clutch element is rotatable relative to the rotation element, particularly during dose-setting. With the clutch closed, the rotation element is rotationally fixed relative to the clutch element, so that the rotation element follows a rotational movement of the clutch element. To form this clutch, the clutch element can have a first clutch structure and the rotation element can have a second clutch structure, which is disengaged when the clutch is opened and is engaged with the first clutch structure when the clutch is closed. The clutch can be a dog clutch. The first clutch structure and the second clutch structure can each have toothing, the teeth of which can engage with one another to form a rotationally fixed connection. For example, the first clutch structure is an external toothing at the proximal end of the rotation element. For example, the second clutch structure is an internal toothing on the sleeve-like clutch element.

The driving and dosing device can have a second clutch, for example, more particularly a dosing clutch, which is closed when the actuating element is not actuated and opened when the actuating element has been actuated, or is opened by the actuation of the actuating element. With the clutch opened, the clutch element is rotatable relative to the dosing element, particularly during product discharging. With the clutch closed, the dosing element is rotationally fixed relative to the clutch element, so that the clutch element follows a rotational movement of the rotation element. To form this clutch, the clutch element can have a third clutch structure and the dosing element can have a fourth clutch structure, which is disengaged when the clutch is opened and is engaged with the third clutch structure when the clutch is closed. The clutch can be a dog clutch. The third clutch structure and the fourth clutch structure can each have toothing, the teeth of which can engage with one another to form a rotationally fixed connection. For example, the third clutch structure is an external toothing on the periphery of the clutch element. For example, the fourth clutch structure is an internal toothing on the sleeve-like dosing element.

It is particularly advantageous if the clutch element is already rotationally fixedly coupled to the rotation element by means of the first clutch and is still rotationally fixedly connected to the dosing element by means of the second clutch while the actuating element is being pushed for actuation onto the housing. This ensures that the clutch element is coupled securely to the rotation element when the clutch element has been released for a rotation relative to the housing of the dosing element. In other words, there is an intermediate position between the completely actuated position and the non-actuated position of the actuating element, in which the clutch element is both coupled rotationally fixedly to the dosing element and also rotationally fixedly to the rotation element.

The driving and dosing device can have a third clutch, for example, which is closed when the actuating element is non-actuated and opened when the actuating element has been actuated, or is opened by the actuation of the actuating element. This clutch couples the rotation element torsion-freely to the housing when the clutch is closed, i.e. the actuating element has not been actuated, while the clutch can be disengaged or opened by actuating the actuating element, so that the rotation element is rotatable relative to the housing.

To form this clutch, the rotation element can have a fifth clutch structure and the dosing element can have a sixth clutch structure, which is disengaged when the clutch is opened and is engaged with the fifth clutch structure when the clutch is closed. The clutch can be a dog clutch. The fifth clutch structure and the sixth clutch structure can each have toothing, the teeth of which can engage with one another to form a rotationally fixed connection. For example, the fifth clutch structure is an external toothing on the periphery of the rotation element. For example, the sixth clutch is an internal toothing on the housing or an element fixed relative to the housing.

It is particularly advantageous if—while the actuating element is being displaced for actuation relative to the housing—the third clutch is only opened if the first clutch is closed and the second clutch is open.

The driving and dosing device can optionally have a ratchet element, particularly a ratchet sleeve. The ratchet element is preferably rotationally fixedly connected to one end of the drive spring; in particular, the end of the spring is fixed to the ratchet element. Thus the discharge spring can be rotationally fixedly supported at one end, more particularly its proximal end, on the ratchet element. The ratchet element can have, or more particularly form, a first resiliently arranged catch element and a second resiliently arranged catch element. The ratchet sleeve is preferably arranged between the rotation element and the clutch element. The first catch element can be in a first interlocking engagement with the clutch element, more particularly internal teeth of the clutch element, which transmits a rotational movement of the clutch element in one rotational direction, more particularly the rotational direction that causes a cocking of the spring, and does not transmit it in the opposite rotational direction, which would cause relaxation of the spring. The effect of this is that a rotation of the dosing element cannot relax the drive spring. The second catch element can be in a second interlocking engagement with the rotation element, more particularly external teeth of the rotation element, which permits a rotational movement of the ratchet element relative to the rotation element in one rotation direction, more particularly in the rotational direction that causes cocking of the spring, and blocks the rotation in the opposite direction of rotation, more particularly the rotational direction in which the rotation element turns for discharging the product. The effect of this is that the spring outputs its torque for discharging the product to the rotational element via the ratchet element and the second interlocking engagement.

The first interlocking engagement is preferably designed such that the clutch element is rotatable relative to the ratchet element when turned in the rotational direction that would cause cocking of the spring if the drive spring is sufficiently cocked that a threshold torque has been reached, or if the drive spring is completely cocked. In this way, the device is protected from damage due to an excessively cocked spring on the one hand, and on the other, it is ensured that dosing, i.e. rotation of the dosing element, is still possible even if the drive spring is completely cocked.

In generally preferred embodiments, the dose indicating element can have a stop, such as a zero dose stop, which is moved away from a mating stop, in particular a mating zero dose stop, whenever a dose is increased and is moved toward the mating stop whenever a dose is reduced, or when the device is actuated for discharging the set product dose.

In advantageous refinements, the driving and dosing device can comprise a mechanism for preventing the setting of a dose that exceeds the quantity of a medication in the product container. In particular, this mechanism can block rotation of the dosing element in a direction that would cause an increase of the dose, more particularly even if the maximum stop of the dose indicating element and the maximum dose mating stop are not yet engaged or if a dose is displayed in the pointing device that is smaller than the maximum adjustable product dose. The mechanism thus prevents setting a dose that exceeds the remaining amount of product contained in the product container, which reduces the danger of misuse of the driving and dosing device. The mechanism can have a limiter, for example, which is positioned between two parts, of which one rotates relative to the other during dose-setting and does not rotate during actuation, i.e. dose discharging. For example, the limiter can be arranged between the dose-setting element, which can be designed in particular as a dose-setting knob or dose-setting sleeve, and the housing or an element fixed in relation to the housing. The limiter, the dose-setting element and the housing can be coupled to one another in such a manner that a relative rotation, particularly during dose-setting, between the dose-setting element and the housing causes the limiter to move to a stop position in which the limiter prevents setting a dose that exceeds the amount of a product in the product container. Examples of appropriately suitable limiters are disclosed in WO 2010/149209 A1 or in WO 01/19434 A1, particularly in FIG. 3 thereof. For example, the limiter can have an internal thread that is engaged with an external thread of the housing. In particular, the limiter can have a longitudinal guide on its outer side by which it is engaged with the dose-setting element such that the dose-setting element is rotationally fixed relative to the limiter. Alternatively, the housing can have the longitudinal guide for the limiter, so that the limiter is rotationally fixed relative to the housing and the limiter can have a thread, particularly an external thread, that engages with a thread, particularly an internal thread, of the dose-setting element.

The stop position is defined by a stop for the limiter, wherein the stop can be formed by the housing or the dose-setting element or a means fixed relative to the housing at least axially or in the circumferential direction. If the limiter and the stop are in contact, a rotation of the dose-setting element in a direction that would cause an increase of the dose is no longer possible or is blocked.

In generally preferred refinements, the driving and dosing device can have at least one signal generation mechanism, such as the ratchet formed between the rotation element and the housing or the element fixed to the housing, the ratchet being adapted to produce, more particularly mechanically produce, an acoustic and/or tactile signal during dose-setting and/or discharging of the product. Such a signal can be perceived as a click signal. For example a (first) signal generation mechanism can be provided, which generates the signal during the dose-setting and can optionally be referred to as a dose-setting signal generation mechanism. In addition, a further (second) signal generation mechanism can be provided, which generates the signal during the product discharging and can optionally be referred to as a product discharge signal generation mechanism. Alternatively, a (common) signal generation mechanism can be provided, which generates a signal during dose-setting and during product discharging.

In general, the signal generation mechanism can be arranged between two parts that move, more particularly rotate, relative to one another during dose-setting or/and product discharging. One of the parts can have a resiliently arranged catch element for example, which engages with a toothing of the other one of the two parts, arranged across the periphery thereof, for example. If one part is moved relative to the other, the catch element can slide over the toothing and generate the signal. The toothing can be formed by an internal periphery or external periphery or an end face of the part.

BRIEF DESCRIPTION OF THE DRAWINGS

FIGS. 2a-d show the driving and dosing device from FIG. 1 in an initial or delivery state, wherein FIG. 2b is a sectional view of FIG. 2a and FIG. 2c is a sectional view of FIG. 2a rotated by 90° along the longitudinal axis of the device, FIG. 2d being rotated by 45°.

FIGS. 6a-c show the driving and dosing device from FIG. 5 in an initial or delivery state, wherein FIG. 6b is a sectional view of FIG. 6a and FIG. 6c is a sectional view of FIG. 6a rotated by 90° along longitudinal axis of the device.

FIGS. 7 and 8 show exploded views of the individual parts of a third embodiment of a driving and dosing device according to the invention, wherein FIG. 8 is a sectional view of FIG. 7.

FIGS. 9a-c show the driving and dosing device from FIGS. 7 and 8 in an initial or delivery state, wherein FIG. 9b is a sectional view of FIG. 9a and FIG. 9c is a sectional view of FIG. 9a rotated by 90° along the longitudinal axis of the device.

DETAILED DESCRIPTION

Figure 1:
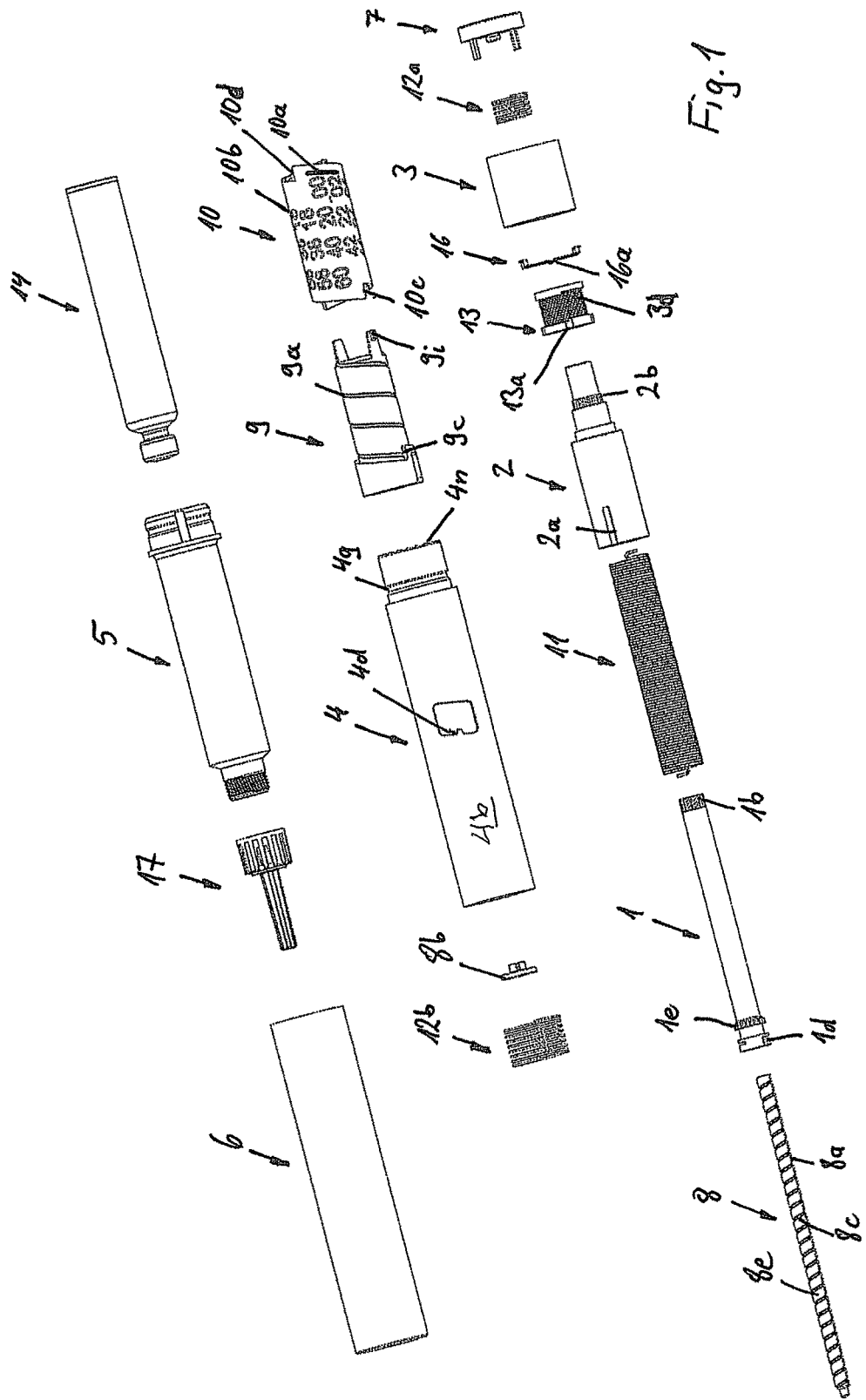
FIG. 1 shows an exploded view of the individual parts of a first embodiment of a driving and dosing device according to the invention.
Figure 2:
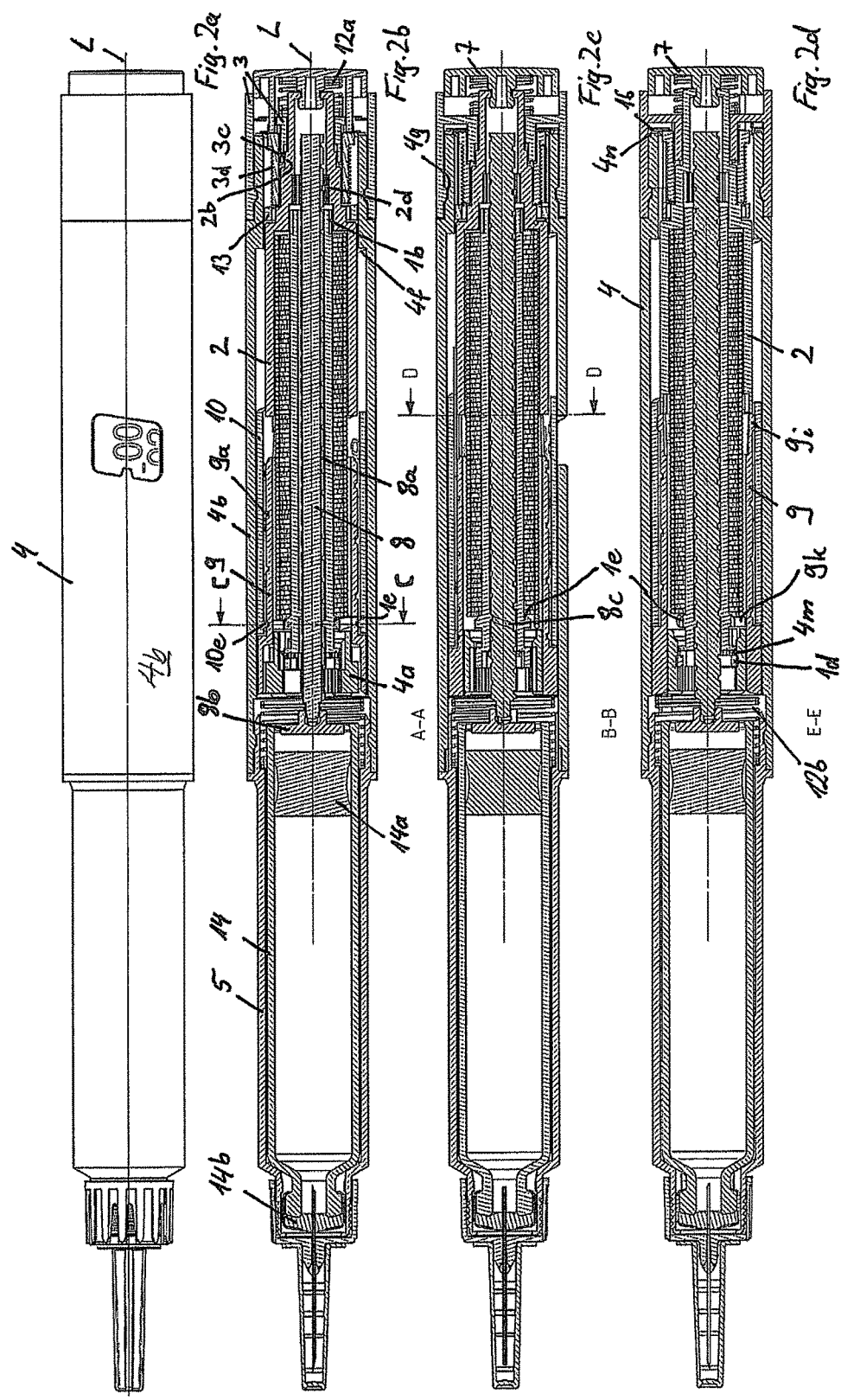
Figure 3:
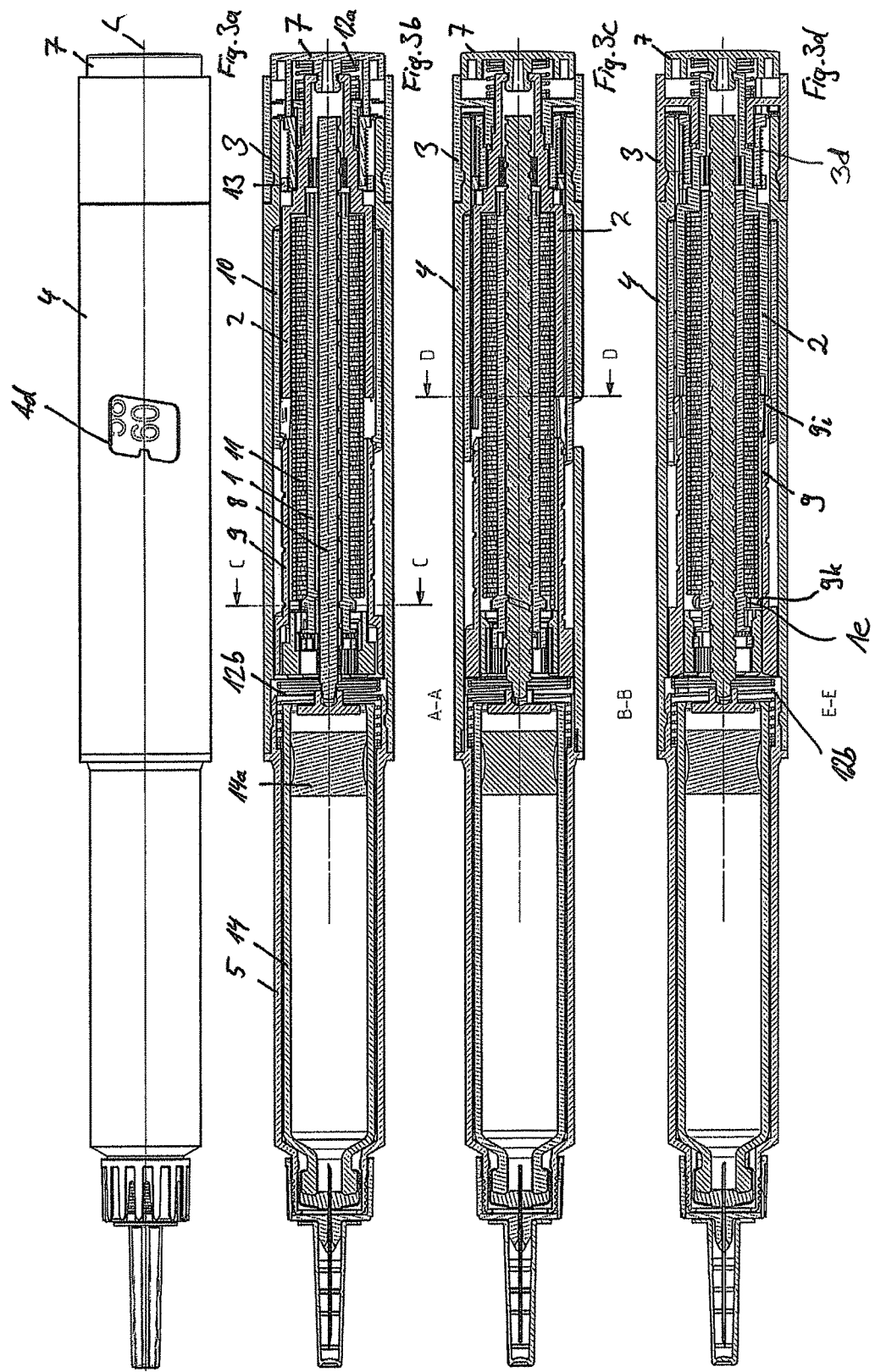
FIGS. 3a-d show the injection device in the views from FIG. 2a-d in a state in which the maximum adjustable dose has been set.
Figure 4:
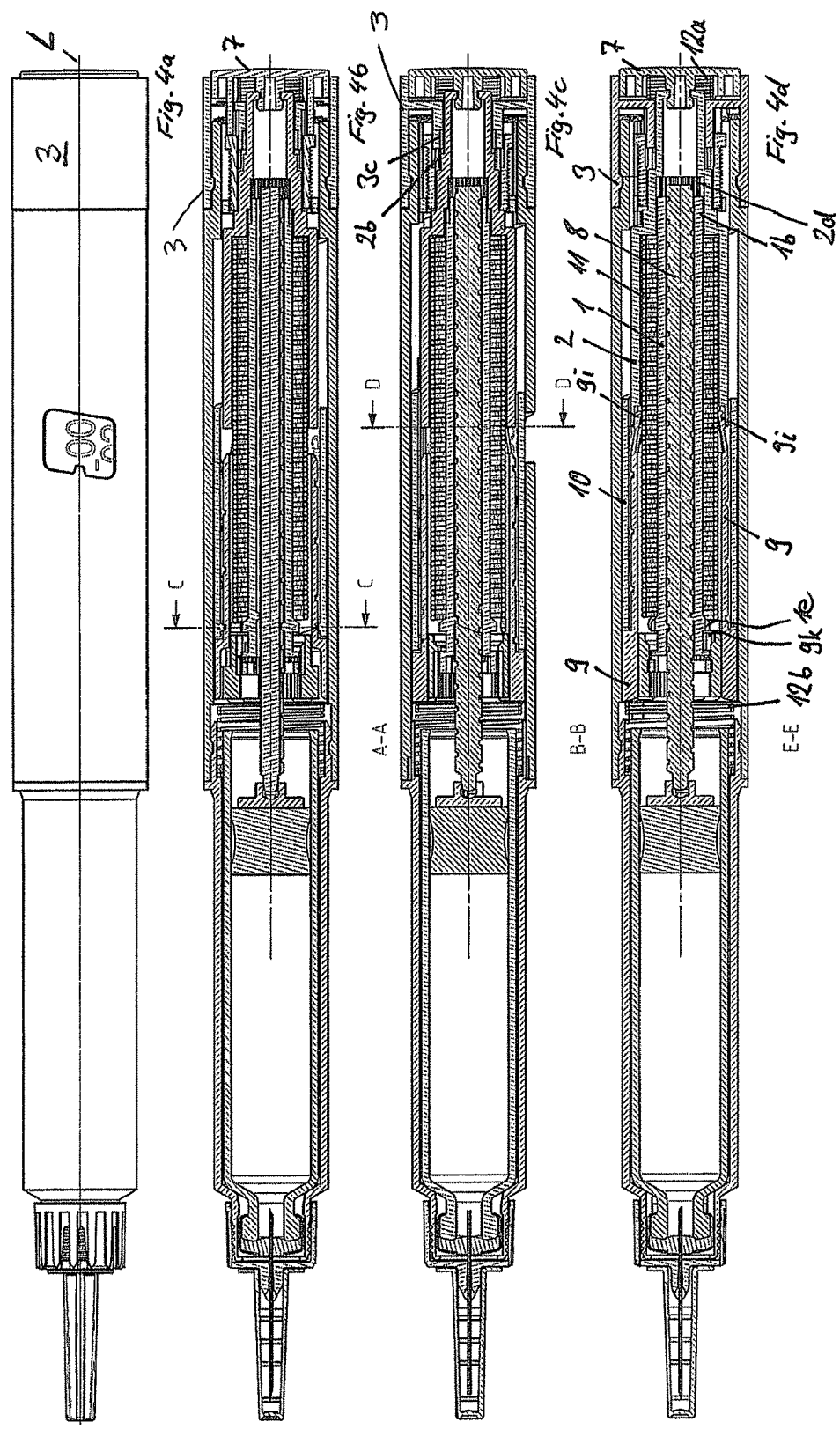
FIGS. 4a-d show the views from FIGS. 2a-d in which the dose set in FIGS. 3a-d has been completely discharged and an actuating element is still being actuated.

In a first embodiment, which is shown in FIGS. 1-4d, the driving and dosing device comprises a sleeve-like housing 4 that has an outer sleeve 4b that can be gripped by the user with one hand. As can be recognized best from FIG. 2b, the housing 4 further comprises an inner sleeve 4a, which forms an abutment for a discharge spring 11 and is arranged concentrically to the outer sleeve 4b. Inner sleeve 4a and outer sleeve 4b are connected to one another via a plurality of webs distributed along the periphery at a distance from one another. An annular gap, through which distal sections of a bearing element 9 protrude, is formed between the outer sleeve 4b and the inner sleeve 4a and is interrupted by the webs. An additional annular gap, in which a dose indicating element 10, formed in particular as a dose indicating drum, i.e. in a sleeve shape, is formed between the bearing element 9 and the outer sleeve 4b.

At the distal end of the housing 4, a sleeve-shaped product container receptacle 5 made from a preferably transparent material is arranged, in which a product container 14 in the form of a carpule is received. The product container 14 is non-detachably connected to the housing 4 by means of the product receptacle 5, so that the driving and dosing device, together with the product container receptacle 5 and the product container 14, forms a disposable injection device, which is, as a whole, disposable after complete emptying of the product container 14. At its distal end, the product container 14 has a septum 14b, which can be penetrated by a needle that can be positioned at the distal end of the product container 14 or the product container receptacle 5. A piston 14a is arranged in the product container 14, wherein the product to be discharged is arranged between the septum 14b and the piston 14a. A displacement of the piston 14a in the direction of the septum, or in the distal direction, i.e. the discharging direction, thus effects a discharge of the product contained in the product container 14. Also shown in FIG. 1 is a protective cap 6, which can be placed over the product container receptacle 5 and is removed before injection of a dose. The needle can be part of a needle unit 17, from which parts such as a needle cover are removed after placement of the needle.

The housing 4, particularly the inner sleeve 4a, is engaged with a propulsion element 8, which can also be referred to as a plunger or a piston rod. The engagement is such that the propulsion element 8 is rotationally fixed relative to the housing 4 and is displaceable axially along the longitudinal axis L. The propulsion element 8 has an external thread 8c and a longitudinal guide 8a such as a longitudinal groove or a flattened area that is overlapped by the external thread 8c. The housing 4 is in torsion-free engagement with the longitudinal guide 8a. An internal thread of a sleeve-shaped rotation element 1 engages with the external thread of the propulsion element 8, the rotation element 1 being arranged or mounted rotatably and axially fixedly in the housing 4. A rotation of the rotation element 1 causes the propulsion element 8 to be displaced along the longitudinal axis L, more particularly in the direction of the piston 14a. The propulsion element 8 is arranged such that its distal end 8d, which is formed by a push-on flange 8b, can act on the piston 14a, in particular can press against the piston 14a.

Around the periphery of the inner sleeve 4a, there is internal toothing 4m, in which a catch element 1d engages, which is arranged resiliently on the periphery of the rotation element 1, more particularly at the distal end thereof. Thereby an acoustic and/or tactile signal, by which it can be recognized that product is being discharged, is generated during the rotation of the rotation element 1 relative to the housing 4. This has the further effect of securing the rotation element 1 against undesired rotations.

The housing 4, more particularly the proximal end of the inner sleeve 4a, forms the abutment for a coil or helical discharge spring 11, which is fixed at one end on the abutment or the housing 4, and at the other, opposite, end on a clutch element 2 rotatable relative to the housing 4. By rotating the clutch element 2 in a first rotation direction relative to the housing 4, the discharge spring 11 is cocked, while the discharge spring 11 is relaxed by rotation of the clutch element 2 relative to the housing 4 in a second rotation direction opposite the first rotational direction. The cocked discharge spring 11 can rotationally drive the clutch element 2 in the second rotational direction by means of the stored spring energy. The spring 11 therefore operates as a torsion spring.

The clutch element 2 is sleeve-shaped. Between the clutch element 2 and the rotation element 1, a first clutch 1b, 2d is arranged, which connects the clutch element 2 and the rotation element 1 rotationally fixedly to one another if an actuating element 7, arranged at the proximal end of the driving and dosing device and configured as an actuating button, is actuated, i.e. pressed by a user of the device (FIGS. 4a-d). The clutch 1b, 2d decouples the clutch element 2 and the rotation 1 element from one another such that the clutch element 2 is rotatable relative to the rotation element 1 whenever the actuating element 7 is not actuated, i.e. not pressed by a user of the device (FIGS. 2a-d, 3a-d). The actuating element 7 is mounted axially fixedly on, more particularly snapped onto, the clutch element 2. By pressing the actuating element 7, the first clutch 1b, 2d is closed, and is opened by releasing the actuating element 7. The first clutch 1b, 2d comprises a second clutch structure 1b, formed on the proximal end of the rotation element 1 by teeth distributed around the outer periphery of the rotation element 1, and a first clutch structure 2d formed by the clutch element 2 by teeth distributed across the inner periphery of the clutch element 2.

The driving and dosing device has a sleeve-shaped dosing element 3, which is rotatably and axially fixedly mounted on the housing 4, and is rotated in the first rotational direction for increasing the dose and/or cocking the spring 11, and in the second rotational direction relative to the housing 4 for reducing the dose and/or relaxing the spring 11.

A second clutch 2b 3c, which connects the dosing element 3 and the clutch element 2 rotationally fixedly to one another when the actuating element 7 is not actuated, is arranged between the dosing element 3 and the clutch element 2 (FIGS. 2a-d, 3a-d). The second clutch 2b, 3c decouples the clutch element 2 and the dosing element 3 from one another so that the clutch element 2 is rotatable relative to the dosing element 3 whenever the actuating element 7 is actuated (FIGS. 4a-d). By pressing the actuating element 7, the second clutch 2b, 3c is closed, and is opened by releasing the actuating element 7. The second clutch 2b, 3c comprises a third clutch structure 2b, formed by the clutch element 2 with teeth 2b distributed across the outer periphery of the clutch element 2, and a fourth clutch structure 3c formed by the dosing element 3 with teeth distributed around the inner periphery of the clutch element 2.

Between the completely actuated position and the non-actuated position of the actuating element 7, the clutch element 2 can occupy an intermediate position, in which both the clutch 2b, 3c and the first clutch 1b, 2d are engaged, i.e. closed. This ensures that the second clutch 2b, 3c only disengages, i.e. is opened, if the first clutch 1b, 2d is engaged, i.e. closed.

The rotation element 1 has a fifth clutch structure in the form of external toothing 1e arranged around the periphery. Together with a sixth clutch structure 9k, which is formed by the bearing element 9, the fifth clutch structure 1e forms a third clutch 1e, 9k. The reference character for the sixth clutch structure 9k is drawn in the figures at the appropriate point (cross section line C-C) although the sixth clutch structure 9k cannot be recognized directly due to the selection of cross-sectional views. The sixth clutch structure 9k is formed by inward-projecting wing-like protrusions of the bearing element 9. The third clutch 1e, 9k connects the rotation element 1 and the housing 4 and/or the bearing element 9 rotationally fixedly to one another if the actuating member 7 is not actuated (FIGS. 2a-d, 3a-d). When the actuating element 7 is actuated, the second clutch 1e, 9k decouples the rotation element 1 and the bearing element 9 from one another so that the rotation element 1 is rotatable relative to the housing 4 and the dosing element 9 (FIGS. 4a-d). The third clutch 1e, 9k is opened by pressing the actuating element 7 and is closed by releasing the actuating element 7, the bearing element 9 being displaced relative to the rotation element 1 along the longitudinal axis L.

A reset spring 12a functioning as a compression spring acts on the actuating element 7, and resets the actuating element 7 or returns it into the non-actuated position when the actuating element 7 is released. The reset spring 12a is supported at one end on the dosing element 3 and the other on the actuating element 7. The reset spring 12a is cocked by pressing the actuating element 7 and is relaxed by releasing it.

The discharge spring 11 can be slightly preloaded at delivery, i.e. in the initial state of the driving and dosing device (FIGS. 2a-d). By turning the dosing element 3 in the first rotational direction, the discharge spring 11 is loaded with sufficient energy that the energy stored in the discharge spring 11 is able to completely discharge the set product dose.

A ratchet spring 16, which makes a rotation of the dosing element 3 relative to the housing 4 more difficult with an inhibiting torque, acts between the housing 4 and the dosing element, the inhibiting torque being higher than the maximum torque transmitted by the maximally preloaded discharge spring 10 to the dosing element 2. This ensures that the discharge spring 11 cannot turn the dosing element 2 back when released. The ratchet spring 16 also has the effect of generating an acoustic and/or tactile signal during dose-setting.

The ratchet spring 16, preferably formed as a punched part, has at least one engagement cam 16a, which engages with front toothing 4n of the housing 4. The ratchet spring 16 is preferably mounted rotationally fixedly on the dosing element 3. During rotation of the dosing element 3 relative to the housing 4, the engagement cams 16a snap over the teeth of the front toothing 4n on the housing 4. The teeth of the toothing 4n are distributed around the periphery at a distance from one another such that each snapping step is proportional to the dose, more particularly corresponds to 1 or 2 IU.

By rotating the clutch element 2 and the rotation element 1 coupled thereto relative to the housing 4 and the propulsion element 8, the spring 11 can displace the propulsion element 8 by a discharge stroke in the distal direction that is proportional to the angle of rotation of the rotation element 1. By selectively blocking and releasing the rotation element 1, which can be accomplished by actuating an actuation element 7, the movement of the propulsion element 8 relative to the housing 4, i.e. the discharge stroke of the propulsion element 8, can be controlled in an advantageous manner.

The bearing element 9, which can also be referred to as an indicating drum bearing element, is arranged rotationally fixedly relative to the housing 4 but displaceably along the longitudinal axis L. The bearing element 9 is engaged with the housing 4, particularly in the annular gap between the inner sleeve 4a and the outer sleeve 4b, which permits a longitudinal movement of the bearing element 9 relative to the housing 4, but prevents a rotational movement. The engagement can be formed by a longitudinal guide between the bearing element 9 and the housing 4.

The bearing element 9 has a thread 9a, in particular an external thread with which a thread 10e, more particularity an internal thread, of the dose indicating element 10 engages. The dose indicating element 10 is screwable relative to the bearing element 9 due to this threaded engagement.

The dose indicating element 10 is rotationally fixedly but axially displaceably connected to the clutch element 2, more particularly engaged therewith. This engagement comprises a longitudinal guide 2a, which causes the dose indicating element 10 to be rotationally fixed relative to the clutch element 2, but axially displaceable. Because of the rotationally fixed connection between clutch element 2 and dose indicating element 10, a rotation of the clutch element 2 relative to the bearing element 9 causes the dose indicating element 10 to likewise be rotated and, due to the threaded engagement with the thread 9a, to be screwed along the bearing element 9, in particular, in addition to the clicking sound produced by the engagement cam 16a.

The dose indicating element 10 has a dose scale 10b comprising a plurality of successively arranged scale values, that extends helically, corresponding to the pitch of the thread 10e, over the outer periphery of the dose indicating element. In the example shown, a maximum dose of 60 IU can be set, the scale extending from 0 to 60 with dose values indicated in increments of two.

Likewise corresponding to the pitch of thread 10e, a marking 10a is arranged in a helical shape over the outer periphery of the dose indicating element 10. This marking 10a is used, as will be described below, to indicate whether the device, or the actuating element 7, is actuated or not actuated. The marking 10a is an optional device. It can extend along the entire dose scale 10b or only parts or only a single scale value. In particular, it is only visible toward the end of product discharging or in the zero position when the driving and dosing device is actuated.

At its distal end, for example, the dose indicating element 10 has a stop surface 10c pointing and acting in the circumferential direction, which is referred to as the zero dose stop. At the proximal end, opposite the distal end, the dose indicating element 10 has a stop surface 10d pointing and acting in the circumferential direction, which is referred to as the maximum dose stop.

The dose indicating element 10 can be screwed back and forth on the bearing element 9 between the zero dose position and the maximum dose position. In the maximum dose position, the maximum dose stop 10d, in connection with the maximum dose mating stop 4f formed in this example by the housing 4, prevents rotation of the dose indicating element 10 in a first rotational direction, namely a rotational direction which would cause an increase of the dose beyond the maximum settable value. In this maximum dose position, the dose indicating element 10 is rotatable in the opposite, i.e. second, rotational direction.

In the zero dose position, shown in FIG. 2b, for example, the zero dose stop 10c, in cooperation with the zero dose mating stop 9c, which is formed by the bearing element 9, prevents rotation of the dose indicating element 10 in the second rotational direction, which would cause the setting of a dose less than zero. Rotation in the first rotational direction is possible in the zero dose position. Although the zero dose mating stop 9c is formed by the bearing element 9, the stop can optionally be formed, differing from the present example, by the housing 4. Differing from the present example, the maximum dose mating stop 4d can be formed by the bearing element 9 or a different part, which is preferably connected rotationally fixedly to the housing 4, however.

The housing 4 has a pointing device 4d in the form of a window, which provides a view of the scale 10b of the dose indicating element 10. The housing 4 has an annular groove 4g, with which, more particularly, an annular shoulder of the dosing element 3 engages for a rotatable and axially fixed connection. The dosing element 3 can have a grip structure across its periphery, which makes it easier for the user of the device to rotate the dosing element 3 relative to the housing 4. In the non-actuated state of the actuating member, a rotation of the dosing element 3 causes a rotation or helical movement of the dose indicating element 10 in addition to the change in the tension of the discharge spring 11, whereby the desired dose can be set and read out in the pointing device 4d.

The actuating element 7 is movable relative to the dosing element 3 along the longitudinal axis L in order to actuate the device for discharging a product. The actuating element 7 forms the proximal end of the device and can be actuated, in particular displaced relative to the housing 4 and/or the dosing element 3, in an easy manner by the thumb of the hand holding the housing 4.

The clutch element 2, particularly the distal end face thereof, strikes the bearing element, particularly on a catch 9i arranged resiliently at the proximal end of the bearing element 9, whereby the bearing element 9 is carried along by the clutch element 2, i.e. also displaced in the distal direction, during actuation of the actuating element 7, which causes a displacement of the clutch element 2 in the distal direction. The driving and dosing device further comprises a further reset spring 12b, which is cocked during actuation of the actuating element 7 and causes the bearing element 9 to be reset, or displaced in the proximal direction. The second reset spring 12b is preferably supported at its distal end on the product container receptacle 5 or the product container 14, and at its proximal end, preferably on the bearing element 9. The reset springs 12a, 12b are preferably constructed as helical springs or coil springs, acting as compression springs.

Particularly on the inner side of the dose indicating element 10, an elevation or a cam can be provided, which is arranged such that, during rotation of the dose indicating element in the second direction, i.e. when counting down the dose values in the pointing device 4d, the cam or elevation deflects the catch 9i, particularly inward and/or out of colliding engagement with the clutch element 2, shortly before the dose 0 is reached or the zero dose stop 10c engages with the zero dose mating stop 9c, particularly when passing through the dose of 1 IU or 2 IU or more generally a value less than 6 IU, whereby the clutch element 2 no longer strikes against the catch 9i. This has the effect that the bearing element, despite the actuated actuating element 7, is movable in the proximal direction and/or is moved past the collision point at which the clutch element 2 strikes against the catch 9i, particularly with an axial movement in the proximal direction. The bearing element 9 is abruptly displaced or accelerated by the second reset spring 12b in the proximal direction, this movement of the bearing element 9 being stopped by a stop formed by the housing 1. Striking against the stop causes an acoustic or tactile signal, more particularly a clicking sound, which indicates to the user that the discharging of the dose has ended or nearly ended. The bearing element 9 has a mating stop for the stop, the mating stop being formed by a projection that additionally limits the axial movement in the proximal direction.

The dosing element 3 is rotationally fixed relative to the actuating element 7. The actuating element 7 reaches through an inward-pointing shoulder of the dosing element 3. Between the distal end of the actuating element 7 and a step of the clutch element 2, a sleeve with an external thread 3d is enclosed axially fixedly, this sleeve being connected rotationally fixedly to the dosing element 3.

The driving and dosing device has a dose limiter 13, in the form of a ring, a ring segment or a nut, having a thread 13b on its inner periphery that engages with a thread 3d, so that the limiter 13 can be screwed relative to the housing 3. At the outer periphery, the limiter 13 has an engagement element 13a, which engages with a longitudinal guide on the inner periphery of the housing 4, so that the dose limiter 13 is rotationally fixed but axially displaceable relative to the housing 4. A stop projection, from which the limiter 13 has a distance proportional to the maximum product quantity that can be discharged from the product container 14, is formed on the dosing element 3 or the sleeve having the thread 3d. Since the dosing element 3 rotates relative to the housing 4 during dose-setting and is not rotated during a dose discharge, the limiter 13 can form a counting mechanism, which adds the already discharged individual doses and the currently set dose and correspondingly moves closer and closer to the stop projection. A dose increase causes the limiter 13 to be moved toward the stop projection. A dose reduction causes the limiter 13 to be moved away from the stop projection. If the remaining dose indicated in the product container 14 is less than the maximum dose that can be set with the driving and dosing device, the limiter 13 comes into contact with the stop projection, so that a rotation of the dosing element 3 relative to the housing 4 in a rotational direction that would result in an increase of the dose (first rotational direction) is blocked.

Particularly because the second clutch 2b, 3c and the third clutch 1e, 9k are open, the discharge spring 11 can relax, the clutch element 2 being rotated relative to the housing 4. The rotation element 1 is rotated with the clutch element 2 due to the closed first clutch 1b, 2d. Due to the rotationally fixed engagement between the clutch element 2 and the dose indicating element 10, the dose indicating element is likewise rotated along with the clutch element 2, whereby the dose indicating element 10 is screwed back into its zero dose position and the propulsion element 8 is displaced by a discharge stroke in the axial direction relative to the housing 4, proportionally to the distance extending in the circumferential direction between the zero dose stop 10c and the zero dose mating stop 9c. The rotation of the rotation element 1 relative to the housing 4 causes the catch element 1d to snap over the toothing 4m, more particularly in dose-proportional angle steps, and produce the acoustic and/or tactile signal.

FIGS. 2a-2d show the driving and dosing device, which can also be referred to as an injection device, in the initial or delivery state, more particularly the state before first usage. The product dose indicated in the pointing device 4d is 0. Actuation of the actuating element 7 would result in no dose being discharged. The limiter 13 is a distance away from the stop projection that is proportional to the quantity of product contained or injectable in the product container 14, e.g. 300 IU.

To set the product dose, the dose setting element 3 is rotated relative to the housing 4, whereby the clutch element 2 and thus also the dose indicating element 10 are rotated relative to the housing 4 due to the closed second clutch 2b, 3c. In the process, the dose indicating element 10 screws along the bearing element 9 due to the thread engagement of the thread 10e with the thread 9a. The opened first clutch 1b, 2d and the closed third clutch 1e, 9k prevent the rotation element 1 from being rotated along with the dose-setting element 3. In particular, the distance between the zero dose stop 10c and the zero dose mating stop 9c is increased proportionally to the dose shown in the pointing device 4d. During the rotation, an audible and tactile signal is generated due to the snapping of the engagement cam 16a over the front toothing 4n. Finally, the discharge spring 11 is cocked by the clutch element 2 rotating in the first rotational direction and supplied with the energy necessary for product discharging.

FIGS. 3a-3d show the driving and dosing device in a state in which a maximum settable dose has been set, namely 60 IU in this example, which can be read out in the pointing device 4d. A further increase of the dose is not possible due to the interaction, more particularly the contact, of the maximum dose stop 10d with the maximum dose mating stop 4f. As can best be recognized from FIGS. 3b-3d, the dose limiter 13 has been advanced or shifted toward the stop projection corresponding to 60 IU.

To discharge the dose shown for the sake of example in FIG. 3a, the actuating element 7 is actuated, more particularly pressed, i.e. displaced in the distal direction relative to the housing 4 and the dosing element 3, whereby the clutch element 2 and the bearing element 9 as well as the dose indicating element 10 are displaced distally relative to the housing 4, more particularly against the force of the coupling or reset springs 12 (springs 12a, 12b in FIG. 1). Because the dose indicating element 10 is displaced axially relative to the housing 4 and the pointing device 4d, the marking 10a shown in FIG. 1 appears in the pointing device 4d, whereby the user can read visually that the device has been actuated. The displacement of the dose indicating element 10 relative to the housing 4 and the pointing device 4d moves the marking 10a along the longitudinal axis L from a position in which it is concealed by the housing 4 into a position in which it is shown in the pointing device 14d.

The actuation of the actuating element 7 has the further effect that the first clutch structure 2d engages with the second clutch structure 1b, i.e. the second clutch 1b, 2d closes, the third clutch structure 2b disengages from the fourth clutch structure 3c, i.e. the second clutch 2b, 3c opens, and the sixth clutch structure 9k disengages from the fifth clutch structure 1e, i.e. the third clutch 1e, 9k opens, so that the clutch element 2 is no longer rotationally fixed in relation to the housing 4, but is instead rotatable. In the actuated state of the actuating element 7, the rotation element 1, the clutch element 2 and the dose indicating element 10 are connected rotationally fixedly to one another, whereby the rotation element 1, the clutch element 2 and the dose indicating element 10 can rotate jointly relative to the housing 4. Due to the torque of the energy stored in the discharge spring 11 applied to the clutch element 2, the dose indicating element 10 is screwed back on the bearing element 9 in the direction of the zero dose stop, the dose displayed in the pointing device 14d counts down, and the propulsion element 8 is moved indirectly via the rotation element 1 in the distal direction relative to the housing 4 by the discharge stroke, which is proportional to the previously set dose.

Shortly before the dose indicating element 10 has reached its zero position, the catch 9i is deflected by means of the dose indicating element 10, whereby the bearing element 9 is displaced in the proximal direction relative to the clutch element 2 by means of the second reset spring 12b, whereby an audible and tactile signal for the user is generated shortly before or when the zero position is reached.

When the dose indicating element 10 has reached its zero position (FIGS. 4a-4d), the previously set dose or single dose has been discharged. If the user releases the actuating member 7, still shown depressed in FIGS. 4a-4c, the first clutch and/or reset spring 12a resets the actuating element 7 and the clutch element 2 to the positions shown in FIGS. 2a-d. During resetting, the clutch element 2 is displaced in the proximal direction relative to the bearing element 9, whereby the catch 9i can spring back into the position in which the clutch element 2 can strike the catch 9i. During resetting, the aforementioned elements are displaced in the proximal direction relative to the housing 4 or the dosing element 3.

During resetting of the device by means of the first and/or springs 12a, 12b, the first clutch structure 2d is disengaged from the second clutch structure 1b and the third clutch structure 2b engages with the fourth clutch structure 3c and the sixth clutch structure 9k engages with the fifth clutch structure 1e. The clutch element 2 is now again rotationally fixed in relation to the dosing element 3, the dosing element 3 again being rotatable together with the dose indicating element 10 relative to the housing 4 and/or the pointing device 4d and/or the rotation element 1 for another setting of a product dose or single dose.

After a number of discharges in this manner, the limiter 13 assumes its stop position (not shown), i.e. it strikes against the stop projection, whereby the limiter 13 blocks the setting of a dose to a value that exceeds the remaining quantity contained in the product container 14. For example, if only 56 IU are contained in the product container 14, in which a maximum of 60 IU can be set with the dosing device, the limiter 13 already comes into contact with the stop projection at 56 IU, so that the dosing element 3 is blocked from rotating in the first direction, which would cause an increase of the dose. Decreasing the dose, however, is possible by turning the dosing element 3 in the second rotational direction.

After the product container 14 has been fully emptied, for example, the driving and dosing device or injection device is disposed of as a whole. This is therefore a disposable injection device. In principle, however, the driving and dosing devices shown herein can also be used in connection with multiple-use injection devices, in which an empty product container 14 is exchanged for a new one.

Figure 5:
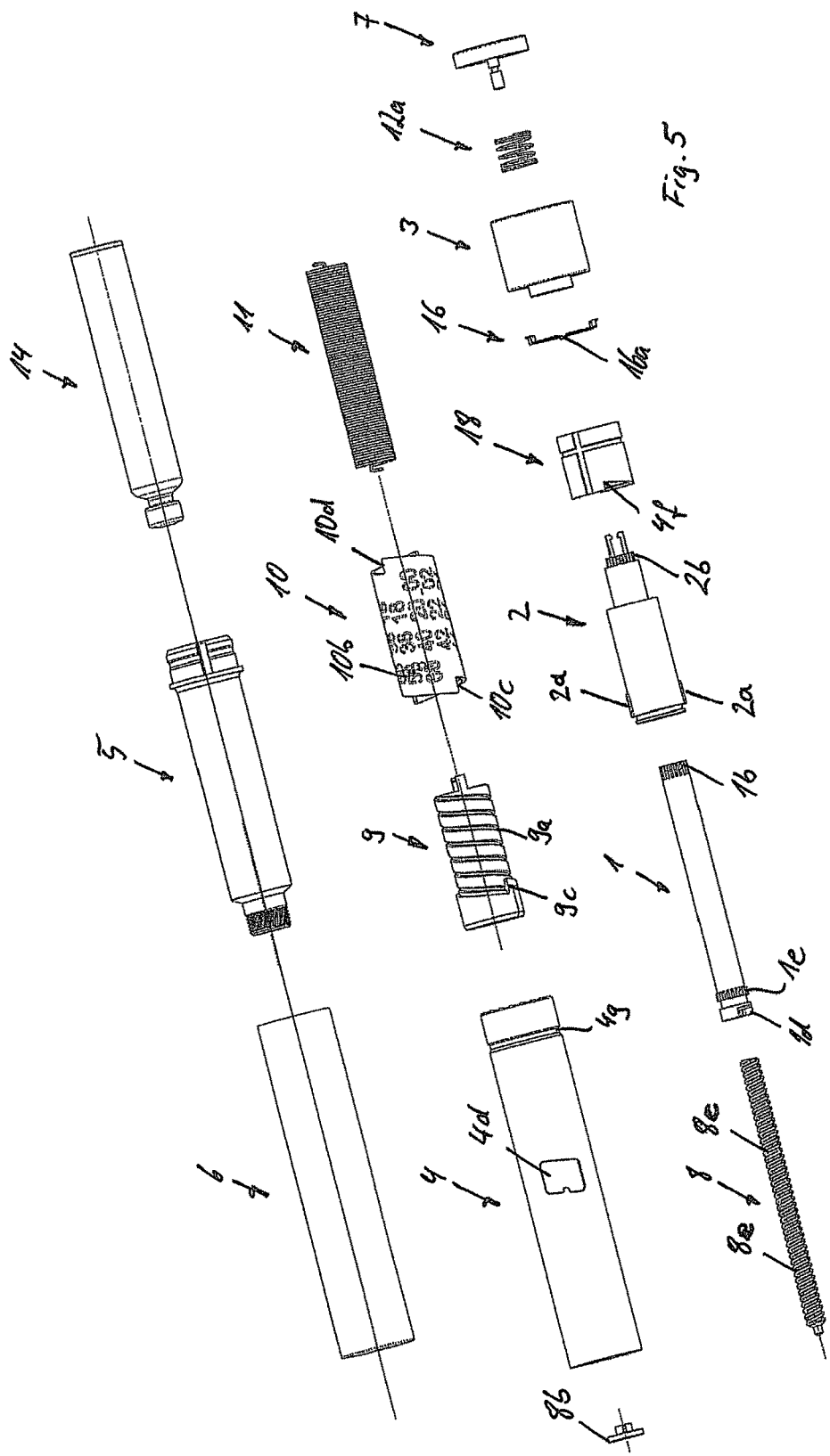
FIG. 5 shows an exploded view of the individual parts of a second embodiment of a driving and dosing device according to the invention.

A second embodiment of a driving and dosing device is shown in FIGS. 5-6c. The features that differ from those of the first embodiment will be described below, and therefore the reader is referred to FIGS. 1-4d in other respects. Identical reference numbers designate parts that are at least functionally equivalent.

The driving and dosing device differs from the embodiment from FIGS. 1-4d particularly in that the clutch element 2 is in an engagement with the bearing element 9 such that the clutch element 2 is rotatable relative to the bearing element 9 and is axially fixed. Thereby the catches 9i can be dispensed with, because a signal that signals reaching the zero dose position during discharging of product is not always necessary. The second reset spring 12b can also be dispensed with in this way, because the first reset spring 12a resets the clutch element 2 and the clutch element 2 drives the bearing element 9 due to the engagement with the bearing element 9.

In addition, the maximum dose mating stop 4f is not formed on the outer housing sleeve 4b but rather on a sleeve 18 fixedly connected rotationally and preferably also axially to the housing sleeve 4b. Not least because of its rotationally and axially fixed engagement with the outer housing sleeve 4b, the sleeve 18 can be considered a part of the housing 4.

Alternatively or additionally, the sleeve 18 forms an internal thread 41 with which an external thread 13b of the limiter 13 engages, the limiter 13 being engaged rotationally fixedly but axially displaceably with the dosing element 3.

The limiter 13 is therefore screwable in relation to the housing 4 or the sleeve 18. At its inner periphery, the limiter 13 has an engagement element that engages with a longitudinal groove of the dosing element 3. A stop projection in the form of an axial stop, from which the limiter 13 has a distance proportional to the maximum product quantity that can be discharged from the product container 14, is formed on the dosing element 3 or the sleeve having the thread 3d (see FIG. 1). Thereby the counting mechanism described in the first embodiment, to which the reader is referred, is formed.

A third embodiment of a driving and dosing device is shown in FIGS. 7-9c. The features that differ from those of the second embodiment will be described below, and therefore the reader is referred to FIGS. 1-6d in other respects. Identical reference numbers designate parts that are at least functionally equivalent.

The driving and dosing device differs from the second embodiment particularly in that the discharge spring 11 is cocked during rotation of the dosing element 3 in the first rotational direction, i.e. increasing the dose, and is not cocked during rotation in a second direction, i.e. during dose reduction. A ratchet element 19, which can also be referred to as a ratchet sleeve, provided for this purpose is kinematically arranged between the discharge spring 11 and the dosing element 3 and transmits a rotation of the dosing element in the first rotational direction to the discharge spring 11, so that the discharge spring 11 is cocked, and does not transmit a rotation in the second rotational direction to the discharge spring 11, i.e. rotationally decouples the dosing sleeve 2 from the drive spring 11, so that the discharge spring 11 is not relaxed.

The proximal end of the discharge spring 11 is mounted secured against torsion on the sleeve-like ratchet element 19. The ratchet element 19 has a first resiliently arranged engagement element 19a, which engages with internal toothing 2e of the clutch element 2, wherein the engagement element 19a cooperates with the internal toothing 2e in such a manner that the ratchet element 19 is rotated along with the clutch element 2 when the clutch 2 is rotated in the first rotational direction, while the clutch element 2 rotates relative to the ratchet element 19 when rotated in the second rotational direction. The internal toothing preferably has sawtooth-shaped teeth, each of which has a shallow and a steep flank, whereby this effect is achieved.

The ratchet element 19 has a second resiliently arranged engagement element 19b, which engages with an external toothing 1f of the rotation element 1, the second engagement element 19b interacting with the external toothing 1f in such a manner that a rotation of the ratchet element 19 relative to the clutch element 2 is possible in the first direction and is not possible, i.e. is blocked, in the second direction. If a dose reduction is undertaken, the clutch element 2 rotates relative to the ratchet element 19, wherein the first engagement element 19a snaps over the internal toothing 2e and the second engagement element 19b is supported rotationally fixedly on the external toothing 1f of the rotation element 1. The closed third clutch 1e, 9k prevents the rotation element 1 from rotating in the second rotational direction. In the example shown, the second clutch structure 1b and the external toothing 1f form toothing jointly, but can of course also be separated from one another.

As described for the other embodiments, the third clutch 1e, 9k is opened for discharging, whereby the discharge spring 11 drives the rotation element 1 in the second rotational direction.

The internal toothing 1b and the first engagement element 19a are matched to one another, particularly by adapting the steep flank of the teeth for the internal toothing 1b, in such a manner that the clutch element 2 drives the ratchet element 19 during rotation in the first rotational direction so long as a certain threshold torque has not been reached, and is rotated relative to the ratchet element 19 when the threshold torque has been reached or exceeded. The threshold torque is selected such that the discharge spring cannot be cocked beyond the linear range of the spring constant, whereby damage to the discharge spring 11 due to excessive cocking is prevented. The ratchet 19 can thus interact with the clutch element 2 according to the principle of a torque-limiting slip clutch.

The invention claimed is:

1. A driving and dosing device for an injection device for administering a liquid product, wherein a product dose to be administered is set with the driving and dosing device, comprising:
   a) a housing;
   b) a dose indicating element, over a periphery of which a dose scale is arranged;
   c) a pointing device and a dosing element, which can be gripped by a user of the driving and dosing device, wherein by rotating the dosing element relative to the pointing device in order to set the dose to be administered, the dose indicating element is rotated or screwed to move relative to the pointing device and about an axis of rotation (L), and a value of the dose scale corresponding to a set dose is readable by means of the pointing device;
   d) a discharge spring, which stores the energy necessary for discharging of the product, wherein the discharge spring is cocked by rotating the dosing element;
   e) an actuating element; and
   f) a first clutch that couples the dosing element to the discharge spring in such a manner that the discharge spring is cocked by rotating the dosing element when the actuating element is not actuated,
      wherein the first clutch comprises a clutch element in a releasable coupling with the dosing element, and
      wherein the first clutch decouples the dosing element from the discharge spring when the actuating element is actuated.

2. A driving and dosing device according to claim 1, further comprising a bearing element, wherein the bearing element engages with the dose indicating element and such engagement causes the rotational or screwing movement of the dose indicating element relative to the pointing device, wherein the bearing element is displaceable together with the dose indicating element relative to the housing and along the axis of rotation (L) in a distal direction.

3. A driving and dosing device according to claim 2, characterized in that the bearing element has a resiliently arranged catch, against which a clutch element strikes at a striking point on an end face, when an actuating element is actuated for discharging a product, wherein the catch is deflected by means of the dose indicating element, whereby the catch is displaced past the striking point axially.

4. A driving and dosing device according to claim 3, characterized in that a reset spring acts on the bearing element, pushing the catch past the striking point, when a dose value less than 2 IU can be read off at the pointing device.

5. A driving and dosing device according to claim 2, characterized in that the bearing element is engaged with a clutch element such that the clutch element is rotatable relative to the bearing element and is axially fixed.

6. A driving and dosing device according to claim 2, further comprising an actuating element, the actuation of which has the effect that the bearing element is displaced together with the dose indicating element relative to the housing and along the axis of rotation (L), and/or that a propulsion element, the distal end of which is provided to act on a piston of a product container that is fixed to the driving and dosing device, is displaced in the distal direction, and the actuation of the actuating element has the further effect that the dose indicating element is rotated or screwed, relative to the bearing element in a direction such that the values of the dose scale passing by the pointing device as the dose indicating element is rotated or screwed count down.

7. A driving and dosing device according to claim 2, wherein actuation of the actuating element actuates two or more clutches associated with a rotation element such that the dose indicating element is engaged to perform a screwing movement relative to the bearing element during dose delivery in a direction causing dosing values to move past the pointing device during the screwing movement thereby to count down on the dose scale.

8. A driving and dosing device according to claim 7, wherein as the count down on the dose scale approaches a value less than 6 IU, the bearing element is abruptly displaced or accelerated by a reset spring for movement in the proximal direction, this movement of the bearing element being stopped by a stop formed by the housing, whereby striking against the stop causes an acoustic or tactile signal.

9. A driving and dosing device according to claim 7, wherein each of at least two or more of the clutches associated with the rotation element comprises teeth distributed around the outer periphery of the rotation element.

10. A driving and dosing device according to claim 1, wherein the first clutch has a clutch element that is connected rotationally fixedly and axially displaceably to the dose indicating element and/or on which one end of the discharge spring is mounted.

11. A driving and dosing device according to claim 10, further comprising a ratchet element that forms a first resiliently arranged catch element and a second resiliently arranged catch element and is connected to one end of the discharge spring, wherein the first catch element has an interlocking engagement with the clutch element that transfers a rotational movement of the clutch element in one rotational direction to the ratchet element and does not transmit it in an opposite rotational direction, and wherein the second catch element has an interlocking engagement with a rotation element that permits a rotational movement of the ratchet element relative to the rotation element in one rotational direction and blocks it in an opposite rotational direction.

12. A driving and dosing device according to claim 11, wherein the actuating element and an additional clutch couples the rotation element secured against torsion to the housing when the actuating element is not actuated, wherein the additional clutch is disengaged by actuating the actuating element, so that the rotation element is rotatable relative to the housing.

13. A driving and dosing device according to claim 11, wherein the discharge spring is a helical or coil spring, wherein a first end of the spring is fixedly connected to the housing and a second end of the spring is rotationally fixedly connected or coupled to the ratchet element.

14. A driving and dosing device according to claim 1, wherein the discharge spring is cocked upon rotation of the dosing element in a first rotational direction, which causes a dose increase, and is relaxed or not relaxed upon rotation of the dosing element in a second rotational direction, which causes a reduction of the dose.

15. A driving and dosing device according to claim 1, further comprising
   an actuating element that is pressed by the user of the driving and dosing device, and is displaced by means of pressing relative to the dosing element in order to discharge the set product dose,
   a propulsion element, the distal end of which is provided to act on a piston of a product container fixed to the dosing and driving device, wherein the propulsion element has a thread and a longitudinal guide,
   a rotation element that engages with either the thread or the longitudinal guide of the propulsion element, the respective other of the elements consisting of thread and longitudinal guide being engaged with the housing or an element fixed relative to the housing, and
   an additional clutch that enables rotation of the rotation element relative to the housing upon pressing of the actuating element and blocks the rotation of the rotation element relative to the housing upon release of the actuating element.

16. A driving and dosing device according to claim 1, wherein the dose indicating element has a stop that is moved away from a mating stop when a dose increase is being performed, and is moved toward the mating stop when a dose reduction is being performed or when the device is actuated for discharging the set product dose.

17. A driving and dosing device according to claim 1, wherein the dose indicating element is at least rotationally decoupled from a rotation element during setting of the product dose, i.e. during increasing and decreasing the dose, and is coupled to the rotation element upon actuation of the device for discharging the product dose.

18. A driving and dosing device according to claim 1, further comprising a ratchet spring with at least one engagement cam that engages with a front toothing of the housing, said ratchet spring being mounted rotationally fixedly on the dosing element such that during rotation of the dosing element relative to the housing, the at least one engagement cam snaps over the teeth of the front toothing.

19. A driving and dosing device for an injection device for administering a liquid product, wherein a product dose to be administered is set with the driving and dosing device, comprising:
   a) a housing;
   b) a dose indicating element, over a periphery of which a dose scale is arranged;
   c) a pointing device and a dosing element, which can be gripped by a user of the driving and dosing device, wherein by rotating the dosing element relative to the pointing device in order to set the dose to be administered, the dose indicating element is rotated or screwed to move relative to the pointing device and about an axis of rotation (L), and a value of the dose scale corresponding to a set dose is readable by means of the pointing device;
   d) a discharge spring, which stores the energy necessary for discharging of the product, wherein the discharge spring is cocked by rotating the dosing element;

e) an actuating element; and
f) a first clutch that couples the dosing element to the discharge spring in such a manner that the discharge spring is cocked by rotating the dosing element when the actuating element is not actuated,
  wherein the first clutch comprises a clutch element in a releasable coupling with the dosing element,
  wherein the first clutch decouples the dosing element from the discharge spring when the actuating element is actuated, and
  wherein the discharge spring is a helical or coil spring, and a first end of the spring is fixedly connected to the housing and a second end of the spring is rotationally fixedly connected or coupled to the dose indicating element, or
  wherein the actuating element is pressed by the user of the driving and dosing device, and is displaced by means of pressing relative to the dosing element in order to discharge the set product dose.

20. A driving and dosing device for an injection device for administering a liquid product, wherein a product dose to be administered is set with the driving and dosing device, comprising:
  a) a housing;
  b) a dose indicating element, over a periphery of which a dose scale is arranged;
  c) a pointing device and a dosing element, which can be gripped by a user of the driving and dosing device, wherein by rotating the dosing element relative to the pointing device in order to set the dose to be administered, the dose indicating element is rotated or screwed to move relative to the pointing device and about an axis of rotation (L), and a value of the dose scale corresponding to a set dose is readable by means of the pointing device;
  d) a discharge spring, which stores the energy necessary for discharging of the product,
    wherein the discharge spring is cocked by rotating the dosing element, and
    wherein the discharge spring is a helical or coil spring, wherein a first end of the spring is fixedly connected to the housing and a second end of the spring is rotationally fixedly connected or coupled to the dose indicating element;
  e) an actuating element, wherein the actuating element is pressed by the user of the driving and dosing device, and is displaced by means of pressing relative to the dosing element in order to discharge the set product dose; and
  f) a first clutch that couples the dosing element to the discharge spring in such a manner that the discharge spring is cocked by rotating the dosing element when the actuating element is not actuated,
    wherein the first clutch comprises a clutch element in a releasable coupling with the dosing element, and
    wherein the first clutch decouples the dosing element from the discharge spring when the actuating element is actuated.

* * * * *